(12) United States Patent
Pfister et al.

(10) Patent No.: US 11,530,366 B2
(45) Date of Patent: Dec. 20, 2022

(54) USE OF VOLATILE COMPOUNDS TO MODULATE THE PERCEPTION OF MUSK

(71) Applicant: Firmenich SA, Satigny (CH)

(72) Inventors: Patrick Pfister, Plainsboro, NJ (US); Matthew Rogers, Plainsboro, NJ (US); Jana Pika, Plainsboro, NJ (US); Florian De Nanteuil, Satigny (CH); Nicholas O'Leary, Plainsboro, NJ (US); Christie Delaura, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/761,795

(22) PCT Filed: Dec. 20, 2018

(86) PCT No.: PCT/EP2018/086381
§ 371 (c)(1),
(2) Date: May 5, 2020

(87) PCT Pub. No.: WO2019/122232
PCT Pub. Date: Jun. 27, 2019

(65) Prior Publication Data
US 2020/0385648 A1 Dec. 10, 2020

Related U.S. Application Data

(60) Provisional application No. 62/609,017, filed on Dec. 21, 2017.

(30) Foreign Application Priority Data

Feb. 20, 2018 (EP) .................................. 18157690

(51) Int. Cl.
*C11B 9/00* (2006.01)
*A61K 8/35* (2006.01)

(52) U.S. Cl.
CPC .............. *C11B 9/0015* (2013.01); *A61K 8/35* (2013.01)

(58) Field of Classification Search
CPC ..................................................... C11B 9/0015
See application file for complete search history.

(56) References Cited

U.S. PATENT DOCUMENTS

2003/0130163 A1   7/2003  Margot
2005/0245407 A1*  11/2005  Ishihara .................. A61Q 5/02
                                                         510/101

(Continued)

FOREIGN PATENT DOCUMENTS

CH        479515 A     10/1969
WO     2015020158 A1    2/2015

OTHER PUBLICATIONS

International Search Report and Written Opinion for International Application No. PCT/EP2018/086381 dated Apr. 9, 2019; 19 pages.

*Primary Examiner* — Arrie L Reuther
(74) *Attorney, Agent, or Firm* — Armstrong Teasdale LLP

(57) ABSTRACT

The various aspects presented herein relate to the perfumery industry. More particularly, the various aspects presented herein relate to compositions and/or ingredients that increase a subjects perception of musk compounds, methods for intensifying a subjects perception of musk compounds, as well as to the perfumed articles or perfuming compositions comprising as an active ingredient, a compound of Formula (I).

6 Claims, 14 Drawing Sheets

(56) References Cited

U.S. PATENT DOCUMENTS

| | | |
|---|---|---|
| 2010/0291016 A1 | 11/2010 | Moretti |
| 2011/0091404 A1 | 4/2011 | Ingo et al. |
| 2012/0184630 A1* | 7/2012 | Kraft ................. C11B 9/003 |
| | | 514/784 |
| 2017/0166836 A1* | 6/2017 | Bedoukian ............ C11B 9/0023 |
| 2017/0362532 A1 | 12/2017 | Pelzer et al. |
| 2018/0245018 A1 | 8/2018 | Vidal et al. |

* cited by examiner

| Odorant Name | EC50 (uM) | | Fold shift |
| --- | --- | --- | --- |
| | -TDA | +TDA | |
| Muscenone | 7.6 | 0.4 | 21x |
| Muscone | 9.4 | 0.7 | 13x |
| Musk C | 0.05 | 0.003 | 16x |
| Musk X | 0.8 | 0.03 | 28x |

Figure 4

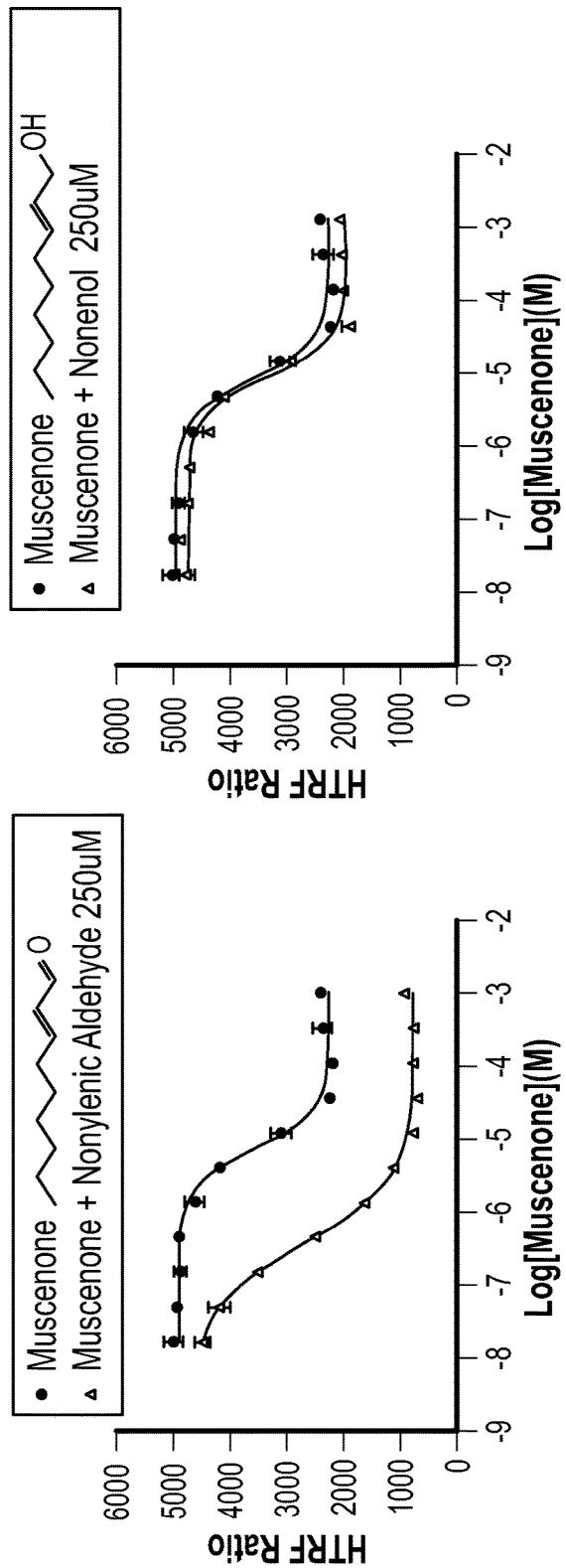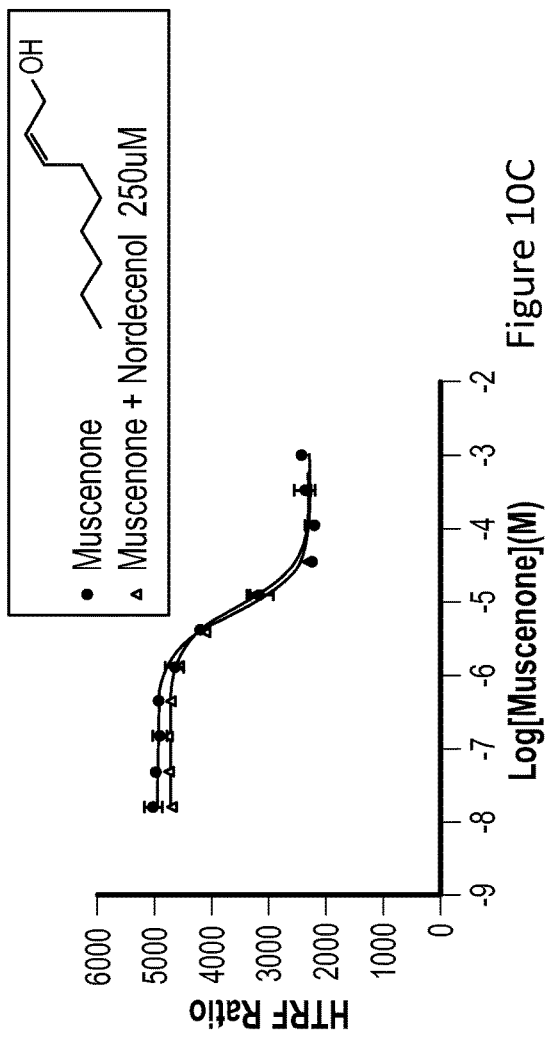
Figure 10A
Figure 10B
Figure 10C

USE OF VOLATILE COMPOUNDS TO MODULATE THE PERCEPTION OF MUSK

CROSS-REFERENCE TO RELATED APPLICATIONS

The present application is the United States national stage application of PCT Application No. PCT/EP2018/086381, filed Dec. 20, 2018, which claims priority to U.S. Provisional Application No. 62/609,017, filed on Dec. 21, 2017, and European Patent Application No. 18157690.1, filed on Feb. 20, 2018, the entire contents of which are hereby incorporated by reference in their entirety.

FIELD OF THE INVENTION

The various aspects presented herein relate to the perfumery industry. More particularly, the various aspects presented herein relate to compositions and/or ingredients that increase a subject's perception of musk compounds, methods for intensifying a subject's perception of musk compounds, as well as to the perfumed articles or perfuming compositions comprising as an active ingredient, a compound of Formula (I).

BACKGROUND

Musk compounds span chemically diverse families of molecules that generate a scent that is highly appreciated in perfumery.

The intensity of the musk scent perceived by a subject is dependent on several factors, such as, but not limited to, the concentration of the musk compound in the perfumed article or perfuming composition, the subject's ability to perceive the musk scent, the efficacy and the affinity to the musk compound for musk olfactory receptors, the particular musk olfactory receptors present in the subject, and the like.

Consequently, there is a need to increase a subject's perception of musk compounds, and/or generate perfumed articles or perfuming compositions wherein the perception of musk is conveyed, enhanced, improved or modified.

SUMMARY

One aspect presented herein provides a method,
wherein the method conveys, enhances, improves or modifies an intensity and/or sensitivity of the perception of a musk odor in a subject in need thereof,
wherein the method comprises contacting the subject with at least one positive allosteric modulator having the structure:

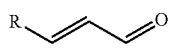
Formula (I)

in the form of any one of its stereoisomers or a mixture thereof,
wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and
wherein the subject is contacted with the at least one positive allosteric modulator in an amount sufficient to convey, enhance, improve or modify the intensity and/or sensitivity of the perception of the musk odor in the subject.

In one aspect, the method further comprises contacting the subject with at least one musk compound.

One aspect presented herein provides a method,
wherein the method increases the potency and/or efficacy of at least one musk compound for a musk olfactory receptor in a subject in need thereof,
wherein the method comprises contacting the subject with at least one positive allosteric modulator having the structure:

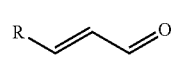
Formula (I)

in the form of any one of its stereoisomers or a mixture thereof,
wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and
wherein the subject is contacted with the at least one positive allosteric modulator in an amount sufficient to increase the potency and/or efficacy of the at least one musk compound for a musk olfactory receptor in the subject.

In one aspect, the method further comprises contacting the subject with at least one musk compound.

In one aspect, the amount sufficient of the at least one positive allosteric modulator increases the potency and/or efficacy for the musk compound for the musk olfactory receptor 2 fold to 30 fold.

In one aspect, the increase in the potency and/or efficacy of the at least one musk compound for the musk olfactory receptor conveys, enhances, improves or modifies an intensity and/or sensitivity of the perception of a musk odor in the subject.

In one aspect, the at least one positive allosteric modulator is incorporated into a perfuming composition.

In one aspect, the perfuming composition further comprises at least one musk compound.

In one aspect, the perfuming composition is incorporated into a consumer product.

In one aspect, the at least one positive allosteric modulator is incorporated into a consumer product.

In one aspect, the consumer product further comprises at least one musk compound.

One aspect presented herein provides a perfuming composition,
wherein the perfuming composition comprises at least one musk compound,
wherein the composition comprises at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans- 5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E, and wherein the amount of the at least one musk olfactory receptor inhibitor in the perfuming composition is below an amount effective to decrease the potency and/or efficacy for the at least one musk compound for a musk olfactory receptor in a subject.

One aspect presented herein provides a perfuming composition, wherein the perfuming composition comprises at least one musk compound, and wherein the composition does not comprise at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E.

One aspect presented herein provides a method, wherein the method conveys, enhances, improves or modifies an intensity and/or sensitivity of the perception of a musk odor of a perfuming composition in a subject in need thereof, wherein the method comprises decreasing the amount of at least one musk olfactory receptor inhibitor in the perfuming composition below an amount effective to decrease the potency for at least one musk compound for a musk olfactory receptor in the subject, and wherein the at least one musk olfactory receptor inhibitor is selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~] hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methyl spiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E.

In one aspect, the perfuming composition comprises at least one musk compound.

In one aspect the decrease of the potency and/or efficacy for the at least one musk compound for a musk olfactory receptor is 1 to 50%.

In one aspect, the perfuming composition is incorporated into a consumer product.

In one aspect, the musk olfactory receptor is the OR5AN1 olfactory receptor.

In one aspect, the at least one musk compound is selected from the group consisting of: muscone, MUSCENONE®, exaltone, exaltenone, exaltolide, habanolide, musk xylol, musk ketone, tonalide, vulcanolide, galaxolide, musk DTI, cashmeran, muscenone delta, romandolide, and helvetolide.

In one aspect, the at least one musk compound is selected from the group consisting of: muscone, muscenone delta, musk xylol, and musk ketone.

One aspect presented herein provides a positive allosteric modulator having the structure:

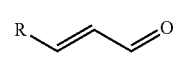

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the compound of Formula (I) is a positive allosteric modulator of a musk olfactory receptor.

In one aspect, the compound of Formula (I) is selected from the group consisting of: (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (Z)-4-(benzyloxy)but-2-enal, (E)-4-(benzyloxy)but-2-enal, (E)-4-cyclohexylidenebut-2-enal, (2E)-3-(4-methylphenyl)-2-propenal, (2E,5E)-6,10-dimethyl-2,5,9-undecatrienal, (2E)-7,8-dimethyl-2,7-nonadienal, methyl (5E)-7-oxo-5-heptenoate, (2E)-7-methyl-2,6-octadienal, (2E)-6,6-dimethyl-2-heptenal, (+−)-(2E)-5,9-dimethyl-2,8-decadienal, (E)-2-tetradecenal, and (E)-8-methoxy-4,8-dimethylnon-2-enal.

One aspect presented herein provides a use of at least one compound of Formula (I) to convey, enhance, improve or modify an intensity and/or sensitivity of the perception of a musk odor of a perfuming composition in a subject in need thereof.

One aspect presented herein provides a use of a perfuming composition comprising at least one compound of Formula (I) to convey, enhance, improve or modify an intensity and/or sensitivity of the perception of a musk odor of a perfuming composition in a subject in need thereof.

One aspect presented herein provides a use of a consumer product comprising at least one compound of Formula (I) to convey, enhance, improve or modify an intensity and/or sensitivity of the perception of a musk odor of a perfuming composition in a subject in need thereof.

One aspect presented herein provides a use of at least one compound of Formula (I) to increase the potency and/or efficacy for at least one musk compound for a musk olfactory receptor in a subject in need thereof.

One aspect presented herein provides a use of a perfuming composition comprising at least one compound of Formula (I) to increase the potency and/or efficacy for at least one musk compound for a musk olfactory receptor in a subject in need thereof.

One aspect presented herein provides a use of a consumer product comprising at least one compound of Formula (I) to increase the potency and/or efficacy for at least one musk compound for a musk olfactory receptor in a subject in need thereof.

In one aspect, the perfuming composition comprises at least one musk compound.

In one aspect, the consumer product comprises at least one musk compound.

In one aspect, the increase in the potency and/or efficacy for the at least one musk compound for the musk olfactory receptor conveys, enhances, improves or modifies an intensity and/or sensitivity of the perception of a musk odor in the subject.

BRIEF DESCRIPTION OF THE FIGURES

FIG. 4 gives the $EC_{50}$ values obtained from the dose response curves obtained in FIG. 3 and summarizes the corresponding the $EC_{50}$ foldshift.

FIG. 10 shows the distinct enhancement levels obtained with nonylenic aldehyde, nonenol and nordecenol, and the absence of enhancement with an alcohol functional group.

DETAILED DESCRIPTION

Figure 1:
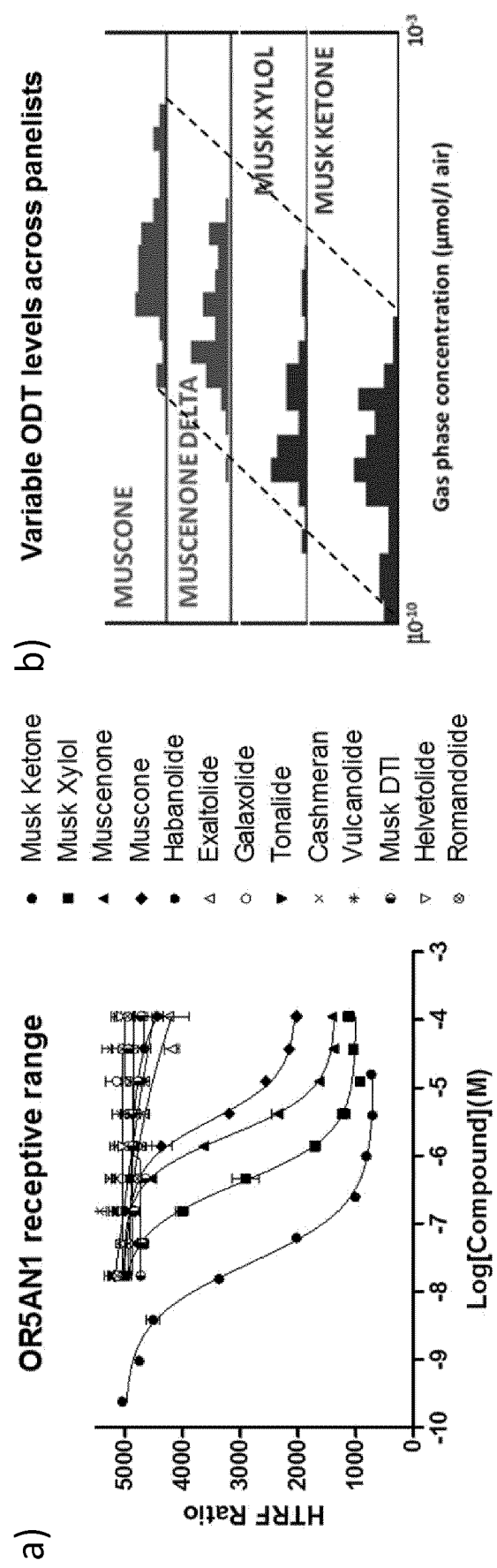
FIG. 1 shows the correlation between musk-induced in vitro levels of OR5AN1 activation recordings for a series of distinct musks (a), and the overall increasing human sensitivities as shown by odor detection threshold recordings of the corresponding musks (b).

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Olfactory receptors (OR) are seven-transmembrane members of the large G-protein coupled receptor (GPCR) family and thus exhibit most pharmacological characteristics of the GPCR receptor family. The present disclosure provides volatile compounds that can be used in perfumery applications to modulate, that is, enhance desired fragrances, such as, for example, a musk odor. In some aspects, volatile compounds that enhance the musk odor are positive allosteric modulators of a musk olfactory receptor. Without intending to be limited to any particular theory, synergistic interaction between perfumery ingredients can lead to more sensitive and more intense perception of perfumery tonalities. Such compounds thus enable new routes to optimize perfumery rules and create better performing commercial perfumery formulations.

The ability of compounds of the present disclosure to modulate the activity of a musk olfactory receptor may be determined by any suitable method readily selected by one of ordinary skill in the art, such as, for example, via an ex vivo cultured neuron assay, or via an in vitro assay using a cell line that expresses a musk olfactory receptor.

Such assays for inhibitors and activators include, e.g., expressing OR family members in cells or cell membranes, applying putative modulator compounds, in the presence or absence of agonists, e.g. musk, and then determining the functional effects on olfactory transduction, as described in the Examples below. Samples or assays comprising OR family members that are treated with a potential inhibitor are compared to control samples without the inhibitor to examine the extent of inhibition. Control samples (untreated with inhibitors, but treated with the agonist) are assigned a relative maximal OR activity value of 100%.

Olfactory receptor activity assays may reveal the following data: (i) whether or not a given compound is an activator of the olfactory receptor or not, and the specificity of the compound for the particular olfactory receptor; (ii) the $EC_{50}$ of an agonist for an olfactory receptor (i.e., the $EC_{50}$ of the agonist); and (iii) the efficacy of an agonist for an olfactory receptor, determined by the amplitude of the response (i.e., the span between baseline and saturated activity levels).

In some aspects, enhanced activation of an OR is achieved when the normalized OR activity value (100%) relative to the agonist control is greater than 100%, for example, about 110%, optionally 120% or 150%, or greater. In one aspect, enhancement of an OR is achieved if the potency of an agonist for the OR in the presence of the enhancer compound is increased. In one aspect, the increase in potency is determined via a shift in the $EC_{50}$ for the agonist. Alternatively, in another aspect, enhancement of an OR is achieved if the $EC_{50}$ value of the agonist in the presence of the enhancer compound is decreased from between 2-fold to 30-fold. In one aspect, enhancement of an OR is achieved if the $EC_{50}$ value of the agonist compound is decreased 2-fold. In another aspect, enhancement of an OR is achieved if the $EC_{50}$ value of the agonist in the presence of the enhancer compound is decreased 30-fold.

In some aspects, enhancement of an OR is achieved if the potency and/or efficacy of an OR agonist in the presence of the enhancer compound is increased relative to the agonist control. In one aspect, enhancement of an OR is achieved if the potency and/or efficacy value of the agonist in the presence of the enhancer compound is increased from between 1.05-fold to 2-fold or greater. In one aspect, enhancement of an OR is achieved if the potency and/or efficacy value of the agonist in the presence of the enhancer compound is increased by about 1.05-fold. In another aspect, enhancement of an OR is achieved if the potency and/or efficacy value of the agonist in the presence of the enhancer compound is increased by about 2-fold.

In one aspect, inhibition of an OR is achieved when the normalized OR activity value (100%) relative to the agonist control is less than 100%, for example, about 80%, optionally 50% or 25-0%. In one aspect, inhibition of an OR is achieved if the potency and/or efficacy of an agonist for the OR is decreased. In another aspect, the decrease in potency and/or efficacy is determined via a shift in the $EC_{50}$ for the agonist. In one aspect, inhibition of an OR is achieved if the $EC_{50}$ value of the agonist in the presence of an antagonist compound is increased from between about 2-fold to aout 30-fold. In one aspect, inhibition of an OR is achieved if the $EC_{50}$ value of the agonist in the presence of the antagonist compound is increased 2-fold. In one aspect, inhibition of an OR is achieved if the $EC_{50}$ value of the agonist in the presence of the antagonist compound is increased 30-fold.

In some aspects, inhibition of an OR is achieved if the potency and/or efficacy of an OR agonist in the presence of the antagonist compound is decreased. In one aspect, inhibition of an OR is achieved if the potency and/or efficacy value of the agonist in the presence of the antagonist compound is decreased from between about 1.25-fold to 4-fold or greater. In one aspect, inhibition of an OR is achieved if the potency and/or efficacy value of the agonist in the presence of the antagonist compound is decreased to 0. In another aspect, inhibition of an OR is achieved if the potency and/or efficacy value of the agonist in the presence of the antagonist compound is decreased 1.25-fold. In one aspect, inhibition of an OR is achieved if the potency and/or efficacy value of the agonist in the presence of the antagonist compound is decreased 4-fold.

As used herein, the term "olfactory receptor", "odorant receptor", or "OR" refers to one or more members of a family of G protein-coupled receptors (GPCRs) that are expressed in olfactory cells. Olfactory receptor cells can also be identified on the basis of morphology or by the expression of proteins specifically expressed in olfactory cells. OR family members may have the ability to act as receptors for odorants and induce an olfactory transduction cascade.

As used herein, the term "orthosteric binding site" refers to the endogenous agonist (odorant ligands in this case) binding site. A binding event to the orthosteric site generally leads to the activation or the inhibition of the receptor's activity.

As used herein, the term "allosteric binding site" refers to a binding site that is topographically distinct from the orthosteric binding site. Allosteric binding in the presence of orthosteric agonist is not sterically hindered and hence occurs in a non-competing fashion. Certain allosteric ligands can act as either positive allosteric modulators (PAMs) or negative allosteric modulators (NAMs) to potentiate or inhibit activation of the receptor by the endogenous agonist, respectively. Other allosteric binding effects also exist which are not discussed here. Positive or negative allosteric modulators enhance or inhibit the effect of the orthosteric ligand, but are largely inactive in the absence of an orthosteric ligand. Allosteric inhibition or enhancement of a receptor's activity can occur by modulating the receptor's conformation and modify 1) the orthosteric site affinity to its agonists, 2) the effect of orthosteric binding activation (e.g. efficacy) or 3) the binding to the G-protein in the case of GPCRs and decrease or increase the signal transduction efficiency, respectively.

As used herein, the term "cooperativity factor" refers to the degree of modulation of an orthosteric ligand binding effect due to the presence of an allosteric ligand.

In some aspects, the present disclosure presents compounds that inhibit or suppress desired odors, such as, for example, a musk odor. In some aspects, the present disclosure provides perfuming compositions and/or consumer products where compounds that or inhibit or suppress desired odors, such as, for example, a musk odor are reduced or removed, resulting in an enhancement of a subject's perception of a musk odor.

Referring to FIG. 1 and Example 1, olfactory receptor OR5AN1 is a human olfactory receptor whose musk-induced activity in vitro correlates with sensory outcome of musk perception. The OR5AN1 olfactory receptor was specifically activated by the musk compounds muscone, MUSCENONE®, musk xylol, and musk ketone, and the observed activation correlated with individuals at the sensory level (FIG. 1). Accordingly, compounds identified via an in vitro screening assay of OR5AN1 activity has a predictive power with respect to the putative sensory outcome and thus represents a good target for musk directed receptor-based enhancement.

Positive Allosteric Modulators of the Musk Olfactory Receptor

Figure 6:
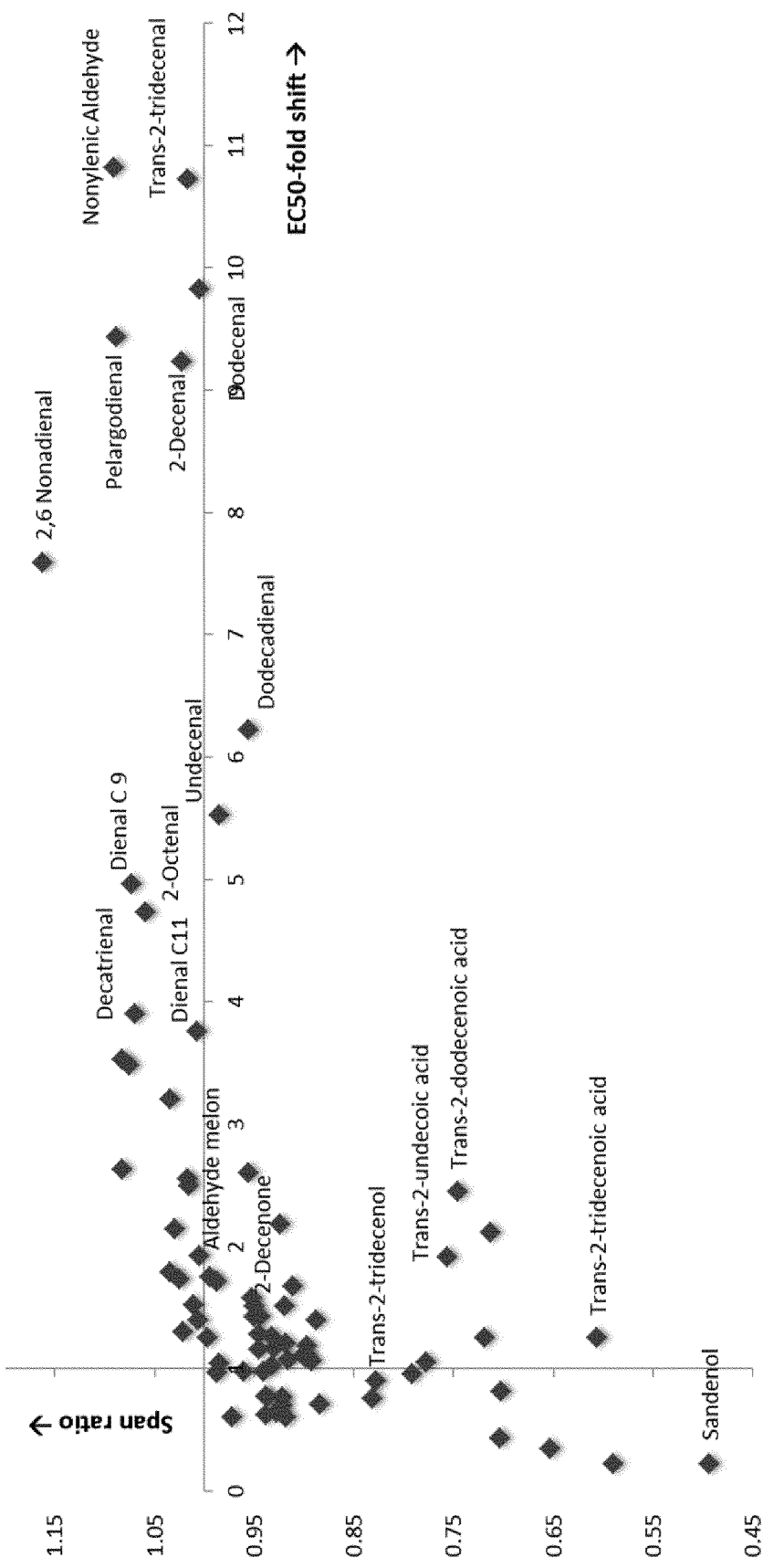
FIG. 6 shows a ranking of 67 volatile compounds according to their OR5AN1 Musk response enhancement capacity based on potency shift and efficacy increase.

Referring to FIG. 6, α-β-mono-unsaturated disubstituted aliphatic aldehydes were systematically found to exhibit potent enhancement of the activity of the OR5AN1 olfactory receptor.

Accordingly, one aspect presented herein provides a positive allosteric modulator having the structure:

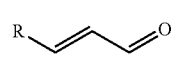

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the compound of Formula (I) is a positive allosteric modulator of a musk olfactory receptor.

For the sake of clarity, by the expression "any one of its stereoisomers", or the similar, it is meant the normal meaning understood by a person skilled in the art, i.e. that the invention compound can be a pure enantiomer (if chiral) or diastereomer (e.g. the double bond is in a conformation E or Z).

According to any one of the above aspect, the compound of Formula (I) can be in the form of its E or Z isomer or of a mixture thereof, e.g. the present disclosure comprises compositions of matter consisting of one or more compounds of Formula (I), having the same chemical structure but differing by the configuration of the double bond. In particular, the compound of Formula (I) can be in the form of a mixture consisting of isomers E and Z and wherein the isomers E represent at least 50% of the total mixture, or even at least 75% (i.e. a mixture E/Z comprised between 75/25 and 100/0).

For the sake of clarity, by the expression "alicyclic alkenyl group", it is meant the normal meaning in the group; i.e. the group has an aliphatic part and a cyclic part and comprises a double bond.

In some aspects, the R group may represent a $C_{3-11}$ linear alkyl group optionally substituted by an ester, a $C_{6-9}$ linear alkenyl or alkadienyl group, a $C_{7-11}$ branched alkenyl or alkadienyl group, a phenyl group substituted by a $C_{1-3}$ alkyl group, a $C_{6-7}$ alicyclic alkenyl group or a benzyloxymethyl group.

In some aspects, the R group may represent a $C_{5-10}$ linear alkyl group, a $C_7$ linear alkyl group substituted by an ester, a $C_{6-9}$ linear alkenyl group, a $C_7$ or a $C_{11}$ branched alkenyl group, a $C_7$ linear or branched alkadienyl group, a $C_{10}$ branched alkadienyl group, a phenyl group substituted by a methyl group, a $C_7$ alicyclic alkenyl group or a benzyloxymethyl group.

In some aspects, the R group may be selected from the group consisting of heptyl group, 3,4-dimethylpent-3-en-1-yl group, hexyl group, decyl group, nonyl group, (Z)-3hexenyl group, (E)-3hexenyl group, 1-nonenyl group, 8-methoxy-8-oxooctyl group, octyl group, 1-hexenyl group, pentyl group, 1-heptenyl group, 1,4-heptadienyl group, octenyl group, 4,8-dimethyl-3-nonenyl group, 3,7-dimthyl-2,6-octadienyl, benzyloxymethyl group, cyclohexylidenemethyl group and para-tolyl group.

In some aspects, the $C_{1-3}$ alkoxy group is a methoxy group.

In one aspect, the compound of Formula (I) is selected from the group consisting of: (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (Z)-4-(benzyloxy)but-2-enal, (E)-4-(benzyloxy)but-2-enal, (E)-4-cyclohexylidenebut-2-enal, (2E)-3-(4-methylphenyl)-2-propenal, (2E,5E)-6,10-dimethyl-2,5,9-undecatrienal, (2E)-7,8-dimethyl-2,7-nonadienal, methyl (5E)-7-oxo-5-heptenoate, (2E)-7-methyl-2,6-octadienal, (2E)-6,6-dimethyl-2-heptenal, (+−)-(2E)-5,9-dimethyl-2,8-decadienal, (E)-2-tetradecenal, and (E)-8-methoxy-4,8-dimethylnon-2-enal.

In some aspects, the compound of Formula (I) may be modified to prolong, modify, increase, or enhance the olfactive and/or musk enhancement benefit provided by the compound of Formula (I). One example of the modification may be to generate a precursor, or profragrance molecule using the compound of Formula (I), wherein the profragrance may release the compound of Formula (I) by a chemical reaction during or after application (using $O_2$, light, enzymes, water (pH) or temperature as the release trigger).

In some aspects, the profragrance does not provide any olfactive and/or musk enhancement benefits.

Examples of methods used to generate a prorragrance are described in International Patent Application Publication No. WO2013/139766.

In some aspects, the profragrance may be a β-thio carbonyl profragrance derivative including, but not limited to: 3-(dodecylthio)-1-(2,6,6-trimethylcyclohex-3-en-1-yl)butan-1-one (derived from δ-damascone, also known and referred to herein as Haloscent® D, trademark and origin: Firmenich SA) or 3-(dodecylthio)-1-(2,6,6-trimethylcyclohex-2-en-1-yl)butan-1-one (derived from 6-damascone) or 4-(dodecylthio)-4-(2,6,6-trimethylcyclohex-2-en-1-yl)butan-2-one (derived from ionone, also known and referred to herein as Haloscent® I, trademark and origin: Firmenich SA), or mixtures thereof.

Another example of a β-thio carbonyl profragrance derivative of formula (I) suitable for use in the present disclosure include the β-thio carbonyl profragrance derivatives disclosed in International Patent Application Publication No. WO2013/032885.

Methods Utilizing Positive Allosteric Modulators of the Musk Olfactory Receptor According to Some Aspects of the Present Disclosure One aspect presented herein provides a use of at least one compound of Formula (I) to convey, enhance, improve or modify an intensity and/or sensitivity of the perception of a musk odor of a perfuming composition in a subject in need thereof. Accordingly, the perfuming composition may comprise at least one musk compound.

One aspect presented herein provides a use of a perfuming composition comprising at least one compound of Formula (I) to convey, enhance, improve or modify an intensity and/or sensitivity of the perception of a musk odor of a perfuming composition in a subject in need thereof.

One aspect presented herein provides a use of a perfuming composition comprising at least one musk compound and at least one compound of Formula (I) to convey, enhance, improve or modify an intensity and/or sensitivity of the perception of a musk odor of a perfuming composition in a subject in need thereof.

One aspect presented herein provides a use of a consumer product comprising at least one compound of Formula (I) to convey, enhance, improve or modify an intensity and/or sensitivity of the perception of a musk odor of a perfuming composition in a subject in need thereof.

One aspect presented herein provides a use of a consumer product composition comprising at least one musk compound and at least one compound of Formula (I) to convey, enhance, improve or modify an intensity and/or sensitivity of the perception of a musk odor of a perfuming composition in a subject in need thereof.

In one aspect, the perfume composition is a pre-formulated perfume composition, and the at least one compound of Formula (I) is added to the pre-formulated perfume composition in an amount sufficient to convey, enhance, improve or modify an intensity and/or sensitivity of the perception of a musk odor of a perfuming composition in the subject.

Some aspects presented herein provides a method,
wherein the method conveys, enhances, improves or modifies an intensity and/or sensitivity of the perception of a musk odor in a subject in need thereof,
wherein the method comprises contacting the subject with at least one positive allosteric modulator having the structure:

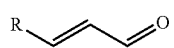

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the subject is contacted with the at least one positive allosteric modulator in an amount sufficient to convey, enhance, improve or modify the intensity and/or sensitivity of the perception of the musk odor in the subject.

In some aspects, the method further comprises contacting the subject with at least one musk compound. The subject may be contacted with the at least one musk compound prior to, simultaneously with, or subsequent to the contacting with the at least one positive allosteric modulator.

Some aspects presented herein provides a method, wherein the method conveys, enhances, improves or modifies an intensity and/or sensitivity of the perception of a musk odor in a subject in need thereof, wherein the method comprises contacting the subject with a perfuming composition comprising at least one positive allosteric modulator having the structure:

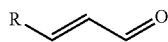

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the subject is contacted with the at least one positive allosteric modulator in an amount sufficient to convey, enhance, improve or modify the intensity and/or sensitivity of the perception of the musk odor in the subject.

In some aspects, the perfuming composition further comprises at least one musk compound.

Some aspects presented herein provides a method, wherein the method conveys, enhances, improves or modifies an intensity and/or sensitivity of the perception of a musk odor in a subject in need thereof, wherein the method comprises contacting the subject with a perfuming composition comprising at least one musk compound and at least one positive allosteric modulator having the structure:

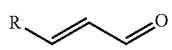

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the subject is contacted with the at least one positive allosteric modulator in an amount sufficient to convey, enhance, improve or modify the intensity and/or sensitivity of the perception of the musk odor in the subject.

One aspect presented herein provides a use of at least one compound of Formula (I) to increase the potency and/or efficacy for at least one musk compound for a musk olfactory receptor in a subject in need thereof.

In some aspects, the increase in potency and/or efficacy for the at least one musk compound for the musk olfactory receptor is determined by a decrease in the $EC_{50}$ for the olfactory receptor activity observed in vitro for the at least one musk compound in the presence of the at least one compound of Formula (I), compared to the $EC_{50}$ for the olfactory receptor activity observed in vitro for the at least one musk compound alone.

One aspect presented herein provides a use of a perfuming composition comprising at least one compound of Formula (I) to increase the potency and/or efficacy for at least one musk compound for a musk olfactory receptor in a subject in need thereof.

One aspect presented herein provides a use of a consumer product comprising at least one compound of Formula (I) to increase the potency and/or efficacy for at least one musk compound for a musk olfactory receptor in a subject in need thereof.

In some aspects, the perfuming composition comprises at least one musk compound.

In some aspects, the consumer product comprises at least one musk compound.

One aspect presented herein provides a use of a perfuming composition comprising at least one musk compound and at least one compound of Formula (I) to increase the potency and/or efficacy for at least one musk compound for a musk olfactory receptor in a subject in need thereof.

One aspect presented herein provides a use of a consumer product composition comprising at least one musk compound and at least one compound of Formula (I) to increase the potency and/or efficacy for at least one musk compound for a musk olfactory receptor in a subject in need thereof.

In one aspect, the increase in the potency and/or efficacy for the at least one musk compound for the musk olfactory receptor conveys, enhances, improves or modifies an intensity and/or sensitivity of the perception of a musk odor in the subject.

In one aspect, the perfume composition is a pre-formulated perfume composition, and the at least one compound of Formula (I) is added to the pre-formulated perfume composition in an amount sufficient to increase the potency and/or efficacy for at least one musk compound for a musk olfactory receptor in the subject.

One aspect presented herein provides a method, wherein the method increases the potency and/or efficacy for at least one musk compound for a musk olfactory receptor in a subject in need thereof, wherein the method comprises contacting the subject with at least one positive allosteric modulator having the structure:

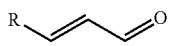

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the subject is contacted with the at least one positive allosteric modulator in an amount sufficient to increase the potency and/or efficacy of the at least one musk compound for a musk olfactory receptor in the subject.

In some aspects, the method further comprises contacting the subject with at least one musk compound. The subject may be contacted with the at least one musk compound prior to, simultaneously with, or subsequent to the contacting with the at least one positive allosteric modulator.

One aspect presented herein provides a method, wherein the method increases the potency and/or efficacy for at least one musk compound for a musk olfactory receptor in a subject in need thereof, wherein the method comprises contacting the subject with a perfuming composition comprising at least one positive allosteric modulator having the structure:

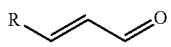

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the subject is contacted with the at least one positive allosteric modulator in an amount sufficient to increase the potency and/or efficacy of the at least one musk compound for a musk olfactory receptor in the subject.

In some aspects, the perfuming composition further comprises at least one musk compound.

Some aspects presented herein provides a method, wherein the method conveys, enhances, improves or modifies an intensity and/or sensitivity of the perception of a musk odor in a subject in need thereof, wherein the method comprises contacting the subject with a perfuming composition comprising at least one musk compound and at least one positive allosteric modulator having the structure:

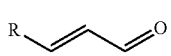

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the subject is contacted with the at least one positive allosteric modulator in an amount sufficient to increase the potency of the at least one musk compound for a musk olfactory receptor in the subject.

In some aspects, the subject is contacted by treating a surface with, or applying to the subject, or dispensing at least partly in the air, the at least one compound of Formula (I).

In some aspects, the at least one positive allosteric modulator is incorporated into a perfuming composition.

In some aspects, the perfuming composition further comprises at least one musk compound.

In some aspects, the perfuming composition is incorporated into a consumer product.

In some aspects, the at least one positive allosteric modulator is incorporated into a consumer product.

In some aspects, the consumer product further comprises at least one musk compound.

In some aspects, the at least one musk compound is selected from the group consisting of: muscone, MUSCENONE®, exaltone, exaltenone, exaltolide, habanolide, musk xylol, musk ketone, tonalide, vulcanolide, galaxolide, musk DTI, cashmeran, muscenone delta, romandolide, and helvetolide.

In some aspects, the at least one musk compound is selected from the group consisting of: muscone, muscenone delta, musk xylol, and musk ketone.

In one aspect, the musk olfactory receptor is the OR5AN1 olfactory receptor.

In some aspects, the amount sufficient of the at least one positive allosteric modulator is from 0.5 to 1000 µM. In some aspects, the amount sufficient of the at least one positive allosteric modulator is from 0.5 to 900 µM. In some aspects, the amount sufficient of the at least one positive allosteric modulator is from 0.5 to 800 µM. In some aspects, the amount sufficient of the at least one positive allosteric modulator is from 0.5 to 700 µM. In some aspects, the amount sufficient of the at least one positive allosteric modulator is from 0.5 to 600 µM. In some aspects, the amount sufficient of the at least one positive allosteric modulator is from 0.5 to 500 µM. In some aspects, the amount sufficient of the at least one positive allosteric modulator is from 0.5 to 400 µM. In some aspects, the amount sufficient of the at least one positive allosteric modulator is from 0.5 to 300 µM. In some aspects, the amount sufficient of the at least one positive allosteric modulator is from 0.5 to 200 µM. In some aspects, the amount sufficient of the at least one positive allosteric modulator is from 0.5 to 100 µM. In some aspects, the amount sufficient of the at least one positive allosteric modulator is from 0.5 to 90 µM. In some aspects, the amount sufficient of the at least one positive allosteric modulator is from 0.5 to 80 µM. In some aspects, the amount sufficient of the at least one positive allosteric modulator is from 0.5 to 70 µM. In some aspects, the amount sufficient of the at least one positive allosteric modulator is from 0.5 to 60 µM. In some aspects, the amount sufficient of the at least one positive allosteric modulator is from 0.5 to 50 µM. In some aspects, the amount sufficient of the at least one positive allosteric modulator is from 0.5 to 40 µM. In some aspects, the amount sufficient of the at least one positive allosteric modulator is from 0.5 to 30 µM. In some aspects, the amount sufficient of the at least one positive allosteric modulator is from 0.5 to 20 µM. In some aspects, the amount sufficient of the at least one positive allosteric modulator is from 0.5 to 10 µM. In some aspects, the amount sufficient of the at least one positive allosteric modulator is from 0.5 to 9 µM. In some aspects, the amount sufficient of the at least one positive allosteric modulator is from 0.5 to 8 µM. In some aspects, the amount sufficient of the at least one positive allosteric modulator is from 0.5 to 7 µM. In some aspects, the amount sufficient of the at least one positive allosteric modulator is from 0.5 to 6 µM. In some aspects, the amount sufficient of the at least one positive allosteric modulator is from 0.5 to 5 µM. In some aspects, the amount sufficient of the at least one positive allosteric modulator is from 0.5 to 4 µM. In some aspects, the amount sufficient of the at least one positive allosteric modulator is from 0.5 to 3 µM. In some aspects, the amount sufficient of the at least one positive allosteric modulator is from 0.5 to 2 µM. In some aspects, the amount sufficient of the at least one positive allosteric modulator is from 0.5 to 1 µM. In some aspects, the amount sufficient of the at least one positive allosteric modulator is from 0.5 to 0.9 µM. In some aspects, the amount sufficient of the at least one positive allosteric modulator is from 0.5 to 0.8 µM. In some aspects, the amount sufficient of the at least one positive allosteric modulator is from 0.5 to 0.7 µM. In some aspects, the amount sufficient of the at least one positive allosteric modulator is from 0.5 to 0.6 µM.

In some aspects, the amount sufficient of the at least one positive allosteric modulator is from 0.6 to 1000 µM. In some aspects, the amount sufficient of the at least one positive allosteric modulator is from 0.7 to 1000 µM. In some aspects, the amount sufficient of the at least one positive allosteric modulator is from 0.8 to 1000 µM. In some aspects, the amount sufficient of the at least one positive allosteric modulator is from 0.9 to 1000 µM. In some aspects, the amount sufficient of the at least one positive allosteric modulator is from 1 to 1000 µM. In some aspects, the amount sufficient of the at least one positive allosteric modulator is from 2 to 1000 µM. In some aspects, the amount sufficient of the at least one positive allosteric modulator is from 3 to 1000 µM. In some aspects, the amount sufficient of the at least one positive allosteric modulator is from 4 to 1000 µM. In some aspects, the amount sufficient of the at least one positive allosteric modulator is from 5 to 1000 µM. In some aspects, the amount sufficient of the at least one positive allosteric modulator is from 6 to 1000 µM. In some aspects, the amount sufficient of the at least one positive allosteric modulator is from 7 to 1000 µM. In some aspects, the amount sufficient of the at least one positive allosteric modulator is from 8 to 1000 µM. In some aspects, the amount sufficient of the at least one positive allosteric modulator is from 9 to 1000 µM. In some aspects, the amount sufficient of the at least one positive allosteric modulator is from 10 to 1000 µM. In some aspects, the amount sufficient of the at least one positive allosteric modulator is from 20 to 1000 µM. In some aspects, the amount sufficient of the at least one positive allosteric modulator is from 30 to 1000 µM. In some aspects, the amount sufficient of the at least one positive allosteric modulator is from 40 to 1000 µM. In some aspects, the amount sufficient of the at least one positive allosteric modulator is from 50 to 1000 µM. In some aspects, the amount sufficient of the at least one positive allosteric modulator is from 60 to 1000 µM. In some aspects, the amount sufficient of the at least one positive allosteric modulator is from 70 to 1000 µM. In some aspects, the amount sufficient of the at least one positive allosteric modulator is from 80 to 1000 µM. In some aspects, the amount sufficient of the at least one positive allosteric modulator is from 90 to 1000 µM. In some aspects, the amount sufficient of the at least one positive allosteric modulator is from 100 to 1000 µM. In some aspects, the amount sufficient of the at least one positive allosteric modulator is from 200 to 1000 µM. In some aspects, the amount sufficient of the at least one positive allosteric modulator is from 300 to 1000 µM. In some aspects, the amount sufficient of the at least one positive allosteric modulator is from 400 to 1000 µM. In some aspects, the amount sufficient of the at least one positive allosteric modulator is from 500 to 1000 µM. In some aspects, the amount sufficient of the at least one positive allosteric modulator is from 600 to 1000 µM. In some aspects, the amount sufficient of the at least one positive allosteric modulator is from 700 to 1000 µM. In some aspects, the amount sufficient of the at least one positive allosteric modulator is from 800 to 1000 µM. In some aspects, the amount sufficient of the at least one positive allosteric modulator is from 900 to 1000 µM.

In some aspects, the amount sufficient of the at least one positive allosteric modulator is from 0.5, or 0.6, or 0.7, or 0.8, or 0.9, or 1, or 2, or 3, or 4, or 5, or 6, or 7, or 8, or 9, or 10, or 20, or 30, or 40, or 50, or 60, or 70, or 80, or 90, or 100, or 200, or 300, or 400, or 500, or 600, or 700, or 800, or 900, or 1000 µM.

In some aspects, the amount sufficient of the at least one positive allosteric modulator increases the potency and/or efficacy for the at least one musk compound for a musk olfactory receptor 2 fold to 100 fold. In some aspects, the amount sufficient of the at least one positive allosteric modulator increases the potency and/or efficacy for the at least one musk compound for a musk olfactory receptor 2 fold to 90 fold. In some aspects, the amount sufficient of the at least one positive allosteric modulator increases the potency and/or efficacy for the at least one musk compound for a musk olfactory receptor 2 fold to 80 fold. In some aspects, the amount sufficient of the at least one positive allosteric modulator increases the potency and/or efficacy for the at least one musk compound for a musk olfactory receptor 2 fold to 70 fold. In some aspects, the amount sufficient of the at least one positive allosteric modulator increases the potency and/or efficacy for the at least one musk compound for a musk olfactory receptor 2 fold to 60 fold. In some aspects, the amount sufficient of the at least one positive allosteric modulator increases the potency and/or efficacy for the at least one musk compound for a musk olfactory receptor 2 fold to 50 fold. In some aspects, the amount sufficient of the at least one positive allosteric modulator increases the potency and/or efficacy for the at least one musk compound for a musk olfactory receptor 2 fold to 40 fold. In some aspects, the amount sufficient of the at least one positive allosteric modulator increases the potency and/or efficacy for the at least one musk compound for a musk olfactory receptor 2 fold to 30 fold. In some aspects, the amount sufficient of the at least one positive allosteric modulator increases the potency and/or efficacy for the at least one musk compound for a musk olfactory receptor 2 fold to 20 fold. In some aspects, the amount sufficient of the at least one positive allosteric modulator increases the potency and/or efficacy for the at least one musk compound for a musk olfactory receptor 2 fold to 19 fold. In some aspects, the amount sufficient of the at least one positive allosteric modulator increases the potency and/or efficacy for the at least one musk compound for a musk olfactory receptor 2 fold to 18 fold. In some aspects, the amount sufficient of the at least one positive allosteric modulator increases the potency and/or efficacy for the at least one musk compound for a musk olfactory receptor 2 fold to 17 fold. In some aspects, the amount sufficient of the at least one positive allosteric modulator increases the potency and/or efficacy for the at least one musk compound for a musk olfactory receptor 2 fold to 16 fold. In some aspects, the amount sufficient of the at least one positive allosteric modulator increases the potency and/or efficacy for the at least one musk compound for a musk olfactory receptor 2 fold to 15 fold. In some aspects, the amount sufficient of the at least one positive allosteric modulator increases the potency and/or efficacy for the at least one musk compound for a musk olfactory receptor 2 fold to 14 fold. In some aspects, the amount sufficient of the at least one positive allosteric modulator increases the potency and/or efficacy for the at least one musk compound for a musk olfactory receptor 2 fold to 13 fold. In some aspects, the amount sufficient of the at least one positive allosteric modulator increases the potency and/or efficacy for the at least one musk compound for a musk olfactory receptor 2 fold to 12 fold. In some aspects, the amount sufficient of the at least one positive allosteric modulator increases the potency and/or efficacy for the at least one musk compound for a musk olfactory receptor 2 fold to 11 fold. In some aspects, the amount sufficient of the at least one positive allosteric modulator increases the potency and/or efficacy for the at least one musk compound for a musk olfactory receptor 2 fold to 10 fold. In some aspects, the amount sufficient of the at least one positive allosteric modulator increases the potency and/or efficacy for the at least one musk compound for a musk olfactory receptor 2 fold to 9 fold. In some aspects, the amount sufficient of the at least one positive allosteric modulator increases the potency and/or efficacy for the at least one musk compound for a musk olfactory receptor 2 fold to 8 fold. In some aspects, the amount sufficient of the at least one positive allosteric modulator increases the potency and/or efficacy for the at least one musk compound for a musk olfactory receptor 2 fold to 7 fold. In some aspects, the amount sufficient of the at least one positive allosteric modulator increases the potency and/or efficacy for the at least one musk compound for a musk olfactory receptor 2 fold to 6 fold. In some aspects, the amount sufficient of the at least one positive allosteric modulator increases the potency and/or efficacy for the at least one musk compound for a musk olfactory receptor 2 fold to 5 fold. In some aspects, the amount sufficient of the at least one positive allosteric modulator increases the potency and/or efficacy for the at least one musk compound for a musk olfactory receptor 2 fold to 4 fold. In some aspects, the amount sufficient of the at least one positive allosteric modulator increases the potency and/or efficacy for the at least one musk compound for a musk olfactory receptor 2 fold to 3 fold.

In some aspects, the amount sufficient of the at least one positive allosteric modulator increases the potency and/or efficacy for the at least one musk compound for a musk olfactory receptor 3 fold to 30 fold. In some aspects, the amount sufficient of the at least one positive allosteric modulator increases the potency and/or efficacy for the at least one musk compound for a musk olfactory receptor 4 fold to 30 fold. In some aspects, the amount sufficient of the at least one positive allosteric modulator increases the potency and/or efficacy for the at least one musk compound for a musk olfactory receptor 5 fold to 30 fold. In some aspects, the amount sufficient of the at least one positive allosteric modulator increases the potency and/or efficacy for the at least one musk compound for a musk olfactory receptor 6 fold to 30 fold. In some aspects, the amount sufficient of the at least one positive allosteric modulator increases the potency and/or efficacy for the at least one musk compound for a musk olfactory receptor 7 fold to 30 fold. In some aspects, the amount sufficient of the at least one positive allosteric modulator increases the potency and/or efficacy for the at least one musk compound for a musk olfactory receptor 8 fold to 30 fold. In some aspects, the amount sufficient of the at least one positive allosteric modulator increases the potency and/or efficacy for the at least one musk compound for a musk olfactory receptor 9 fold to 30 fold. In some aspects, the amount sufficient of the at least one positive allosteric modulator increases the potency and/or efficacy for the at least one musk compound for a musk olfactory receptor 10 fold to 30 fold. In some aspects, the amount sufficient of the at least one positive allosteric modulator increases the potency and/or efficacy for the at least one musk compound for a musk olfactory receptor 11 fold to 30 fold. In some aspects, the amount sufficient of the at least one positive allosteric modulator increases the potency and/or efficacy for the at least one musk compound for a musk olfactory receptor 12 fold to 30 fold. In some aspects, the amount sufficient of the at least one positive allosteric modulator increases the potency and/or efficacy for the at least one musk compound for a musk olfactory receptor 13 fold to 30 fold. In some aspects, the amount sufficient of the at least one positive allosteric modulator increases the potency and/or efficacy for the at least one musk compound for a musk olfactory receptor 14 fold to 30 fold. In some aspects, the amount sufficient of the at least one positive allosteric modulator increases the potency and/or efficacy for the at least one musk compound for a musk olfactory receptor 15 fold to 30 fold. In some aspects, the amount sufficient of the at least one positive allosteric modulator increases the potency and/or efficacy for the at least one musk compound for a musk olfactory receptor 16 fold to 30 fold. In some aspects, the amount sufficient of the at least one positive allosteric modulator increases the potency and/or efficacy for the at least one musk compound for a musk olfactory receptor 17 fold to 30 fold. In some aspects, the amount sufficient of the at least one positive allosteric modulator increases the potency and/or efficacy for the at least one musk compound for a musk olfactory receptor 18 fold to 30 fold. In some aspects, the amount sufficient of the at least one positive allosteric modulator increases the potency and/or efficacy for the at least one musk compound for a musk olfactory receptor 19 fold to 30 fold. In some aspects, the amount sufficient of the at least one positive allosteric modulator increases the potency and/or efficacy for the at least one musk compound for a musk olfactory receptor 20 fold to 30 fold. In some aspects, the amount sufficient of the at least one positive allosteric modulator increases the potency and/or efficacy for the at least one musk compound for a musk olfactory receptor 21 fold to 30 fold. In some aspects, the amount sufficient of the at least one positive allosteric modulator increases the potency and/or efficacy for the at least one musk compound for a musk olfactory receptor 22 fold to 30 fold. In some aspects, the amount sufficient of the at least one positive allosteric modulator increases the potency and/or efficacy for the at least one musk compound for a musk olfactory receptor 23 fold to 30 fold. In some aspects, the amount sufficient of the at least one positive allosteric modulator increases the potency and/or efficacy for the at least one musk compound for a musk olfactory receptor 24 fold to 30 fold. In some aspects, the amount sufficient of the at least one positive allosteric modulator increases the potency and/or efficacy for the at least one musk compound for a musk olfactory receptor 25 fold to 30 fold. In some aspects, the amount sufficient of the at least one positive allosteric modulator increases the potency and/or efficacy for the at least one musk compound for a musk olfactory receptor 26 fold to 30 fold. In some aspects, the amount sufficient of the at least one positive allosteric modulator increases the potency and/or efficacy for the at least one musk compound for a musk olfactory receptor 27 fold to 30 fold. In some aspects, the amount sufficient of the at least one positive allosteric modulator increases the potency and/or efficacy for the at least one musk compound for a musk olfactory receptor 28 fold to 30 fold. In some aspects, the amount sufficient of the at least one positive allosteric modulator increases the potency and/or efficacy for the at least one musk compound for a musk olfactory receptor 29 fold to 30 fold.

In some aspects, the amount sufficient of the at least one positive allosteric modulator increases the potency and/or efficacy for the at least one musk compound for a musk olfactory receptor 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30 fold.

Devices and Applications

In some aspects, the time at which the subject's perception of the musk odor is conveyed, enhanced, improved or modified may be controlled by dispensing at least one compound of Formula (I) at a given time. For example, an at least one musk compound may be dispensed at a first time, and the at least one compound of Formula (I) may be dispensed at a second time.

Accordingly, some aspects presented herein provide a method to convey, enhance, improve or modify an intensity and/or sensitivity of the perception of a musk odor in a subject in need thereof, comprising dispensing sequentially at least partly in the air, at least one musk compound followed by at least one compound of Formula (I).

Alternatively, some aspects presented herein provide a method to convey, enhance, improve or modify an intensity and/or sensitivity of the perception of a musk odor in a subject in need thereof, comprising contacting sequentially the subject with at least one musk compound followed by at least one compound of Formula (I).

Some aspects presented herein provide a method to convey, enhance, improve or modify an intensity and/or sensitivity of the perception of a musk odor in a subject in need thereof, comprising contacting the subject simultaneously with at least one musk compound and at least one compound of Formula (I).

Some aspects presented herein provide a method to convey, enhance, improve or modify an intensity and/or sensitivity of the perception of a musk odor in a subject in need thereof, comprising dispensing simultaneously at least partly in the air at least one musk compound and at least one compound of Formula (I).

Some aspects presented herein provide a method to convey, enhance, improve or modify an intensity and/or sensitivity of the perception of a musk odor in a subject in need thereof, comprising dispensing sequentially at least partly in the air, a perfuming composition comprising at least one musk compound followed by a perfuming composition comprising at least one compound of Formula (I).

Alternatively, some aspects presented herein provide a method to convey, enhance, improve or modify an intensity and/or sensitivity of the perception of a musk odor in a subject in need thereof, comprising contacting sequentially the subject with a perfuming composition comprising at least one musk compound followed by a perfuming composition comprising at least one compound of Formula (I).

Some aspects presented herein provide a method to convey, enhance, improve or modify an intensity and/or sensitivity of the perception of a musk odor in a subject in need thereof, comprising contacting the subject simultaneously with a perfuming composition comprising at least one musk compound and at least one compound of Formula (I).

Some aspects presented herein provide a method to convey, enhance, improve or modify an intensity and/or sensitivity of the perception of a musk odor in a subject in need thereof, comprising dispensing simultaneously at least partly in the air a perfuming composition comprising at least one musk compound and at least one compound of Formula (I).

Accordingly, some aspects presented herein provide a method to increase the potency and/or efficacy for at least one musk compound for a musk olfactory receptor in a subject in need thereof, comprising dispensing sequentially at least partly in the air, at least one musk compound followed by at least one compound of Formula (I).

Alternatively, some aspects presented herein provide a method to increase the potency and/or efficacy for at least one musk compound for a musk olfactory receptor in a subject in need thereof, comprising contacting sequentially the subject with at least one musk compound followed by at least one compound of Formula (I).

Some aspects presented herein provide a method to increase the potency and/or efficacy for at least one musk compound for a musk olfactory receptor in a subject in need thereof, comprising contacting the subject simultaneously with at least one musk compound and at least one compound of Formula (I).

Some aspects presented herein provide a method to increase the potency and/or efficacy for at least one musk compound for a musk olfactory receptor in a subject in need thereof, comprising dispensing simultaneously at least partly in the air at least one musk compound and at least one compound of Formula (I).

Some aspects presented herein provide a method to increase the potency and/or efficacy for at least one musk compound for a musk olfactory receptor in a subject in need thereof, comprising dispensing sequentially at least partly in the air, a perfuming composition comprising at least one musk compound followed by a perfuming composition comprising at least one compound of Formula (I).

Alternatively, some aspects presented herein provide a method to increase the potency and/or efficacy for at least one musk compound for a musk olfactory receptor in a subject in need thereof, comprising contacting sequentially the subject with a perfuming composition comprising at least one musk compound followed by a perfuming composition comprising at least one compound of Formula (I).

Some aspects presented herein provide a method to increase the potency and/or efficacy for at least one musk compound for a musk olfactory receptor in a subject in need thereof, comprising contacting the subject simultaneously with a perfuming composition comprising at least one musk compound and at least one compound of Formula (I).

Some aspects presented herein provide a method to increase the potency and/or efficacy for at least one musk compound for a musk olfactory receptor in a subject in need thereof, comprising dispensing simultaneously at least partly in the air a perfuming composition comprising at least one musk compound and at least one compound of Formula (I).

In some aspects, the sequential dispensing is performed using a device configured to sequentially emanate separate fragrances at timed intervals from each other. Devices suitable for this include the AIRWICK® SYMPHONIA device which is configured to receive two separate bottles of fragrance and sequentially direct heat toward each bottle to accelerate the evaporation of fragrance therefrom. In some aspects, the device configured to sequentially emanate separate fragrances may also emanate a functional composition. Examples of functional compositions include malodor counteracting compositions, insect repellant compositions, and the like.

U.S. Patent Application Publication No. 2013/0156408 A1 discloses an example of a device configured to sequentially emanate separate fragrances at timed intervals from each other.

U.S. Patent Application Publication No. 2013/0156408 A1 discloses an example of methods to sequentially emanate separate fragrances at timed intervals from each other.

U.S. Patent Application Publication No. 2015/0098860 A1 discloses an example of methods to sequentially emanate separate fragrances at timed intervals from each other.

In some aspects, the device comprises dispensing means for dispersing sequentially in the air volatile compositions and a composition as defined in any of the above-described aspects. In some aspects, the device is such that the first accord and the second accord are physically separated by separating means. According to one aspect, the device is an air-freshener. By sequentially diffusing contrasting accords, the intensity of the perfume can be improved over time.

One aspect presented herein provides a manufactured product comprising the perfume composition according to an aspect presented herein. In one aspect, the manufactured product is selected from the group consisting of a perfume, eau de toilette, home care product and a personal care product.

In some aspects, the term "contacting" refers to administering to a subject, a composition as described herein, wherein the administering results in dosing the subject with an effective amount of the compound of Formula (I). Administration may be via any method readily selected by one of ordinary skill in the art. Methods include, but are not limited to, topical administration, inhalation, and the like. Accordingly the present disclosure contemplates formulating a composition comprising a compound of Formula (I) as described herein with a suitable carrier to facilitate administering the a composition comprising a compound of Formula (I) as described herein to the subject.

Alternatively, in some aspects, the term "contacting" refers to dispensing or dispersing a composition comprising a compound of Formula (I) as described herein into a volume in need thereof, wherein the dispensing or dispersing results in dosing the subject with an effective amount of the compound of Formula (I). Dispersion or dispensing of the compound of Formula (I) as described herein may be achieved by any method readily selected by one of ordinary skill in the art. Examples include, but are not limited to, a spray, a nebulizer, evaporation of a solution containing a compound of Formula (I) as described herein, and the like.

Accordingly the present disclosure contemplates formulating a composition comprising a compound of Formula (I) as described herein with a suitable carrier to facilitate treating a surface or volume with a composition comprising a compound of Formula (I) as described herein to the subject.

In some aspects, the term "contacting" refers to contacting a surface of a malodor source with a composition comprising a compound of Formula (I) as described herein, wherein the contacting results in an effective amount of the compound of Formula (I) being deposited on the surface. A composition comprising a compound of Formula (I) as described herein may be contacted on a surface by any method readily selected by one of ordinary skill in the art. Examples include, but are not limited to, a spray, a wipe, a solution, and the like.

Musk Olfactory Receptor Inhibitors

Referring to FIG. 6, the following compounds were found to inhibit the activity of the OR5AN1 olfactory receptor: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butan al, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E.

The terms "antagonists," "inhibitor," "blockers," "suppressors," "counteractants" and "modulators" of olfactory receptors are used interchangeably to refer to inhibitory, blocking, suppressing, or modulating molecules identified using in vivo, ex vivo and in vitro assays for olfactory transduction, e.g., ligands, antagonists, and their homologs and mimetics. Inhibitors are compounds that, e.g., bind to, partially or totally block stimulation, decrease, suppress, prevent, delay activation, inactivate, desensitize, or down regulate olfactory transduction, e.g., antagonists.

Accordingly, one aspect presented herein provides a perfuming composition,
  wherein the perfuming composition comprises at least one musk compound,
  wherein the composition comprises at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E, and
  wherein the amount of the at least one musk olfactory receptor inhibitor in the perfuming composition is below an amount effective to decrease the potency and/or efficacy for the at least one musk compound for a musk olfactory receptor in a subject.

One aspect presented herein provides a perfuming composition,
  wherein the perfuming composition comprises at least one musk compound, and
  wherein the composition does not comprise at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E.

One aspect presented herein provides a method,
wherein the method conveys, enhances, improves or modifies an intensity and/or sensitivity of the perception of a musk odor of a perfuming composition in a subject in need thereof,
wherein the method comprises decreasing the amount of at least one musk olfactory receptor inhibitor in the perfuming composition below an amount effective to decrease the $EC_{50}$ for at least one musk compound for a musk olfactory receptor in the subject, and
wherein the at least one musk olfactory receptor inhibitor is selected from the group consisting of: trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl)acrylaldehyde, sandenol, E-2-butenal, N 302, Z6-nonen-1-ol, 3-phenylpropanal, dartanol=levosandol=one isomer of bacdanol, E2,Z6-nonadien-1-ol, pentyl valerate, decenal Cis 1 Citr, and aldehyde E.

In some aspects, the perfuming composition further comprises at least one musk compound.

In one aspect, the perfuming composition further comprises at least one compound of Formula (I), wherein the at least one compound of Formula (I) is a positive allosteric modulator of a musk olfactory receptor.

In some aspects, when the amount of the at least one musk olfactory receptor inhibitor in the perfuming composition is below an amount effective to decrease the potency and/or efficacy for the at least one musk compound for a musk olfactory receptor in a subject, the subject's perception of the musk odor of the perfuming composition is conveyed, enhanced, improved or modified.

In some aspects, the decrease in the $EC_{50}$ for at least one musk compound for a musk olfactory receptor in the subject is sufficient to convey, enhance, improve or modify the intensity and/or sensitivity of the perception of the musk odor of the perfuming composition in the subject. In some aspects, the decrease of the $EC_{50}$ for the at least one musk compound for a musk olfactory receptor is 4 fold to 0.6 fold. In some aspects, the decrease of the $EC_{50}$ for the at least one musk compound for a musk olfactory receptor is 3.5 fold to 0.6 fold. In some aspects, the decrease of the $EC_{50}$ for the at least one musk compound for a musk olfactory receptor is 3 fold to 0.6 fold. In some aspects, the decrease of the $EC_{50}$ for the at least one musk compound for a musk olfactory receptor is 2.5 fold to 0.6 fold. In some aspects, the decrease of the $EC_{50}$ for the at least one musk compound for a musk olfactory receptor is 2 fold to 0.6 fold. In some aspects, the decrease of the $EC_{50}$ for the at least one musk compound for a musk olfactory receptor is 1.5 fold to 0.6 fold. In some aspects, the decrease of the $EC_{50}$ for the at least one musk compound for a musk olfactory receptor is 1 fold to 0.6 fold. In some aspects, the decrease of the $EC_{50}$ for the at least one musk compound for a musk olfactory receptor is 0.9 fold to 0.6 fold. In some aspects, the decrease of the $EC_{50}$ for the at least one musk compound for a musk olfactory receptor is 0.8 fold to 0.6 fold. In some aspects, the decrease of the $EC_{50}$ for the at least one musk compound for a musk olfactory receptor is 0.7 fold to 0.6 fold.

In some aspects, the decrease of the $EC_{50}$ for the at least one musk compound for a musk olfactory receptor is 4 fold to 0.7 fold. In some aspects, the decrease of the $EC_{50}$ for the at least one musk compound for a musk olfactory receptor is 4 fold to 0.8 fold. In some aspects, the decrease of the $EC_{50}$ for the at least one musk compound for a musk olfactory receptor is 4 fold to 0.9 fold. In some aspects, the decrease of the $EC_{50}$ for the at least one musk compound for a musk olfactory receptor is 4 fold to 1 fold. In some aspects, the decrease of the $EC_{50}$ for the at least one musk compound for a musk olfactory receptor is 4 fold to 1.5 fold. In some aspects, the decrease of the $EC_{50}$ for the at least one musk compound for a musk olfactory receptor is 4 fold to 2 fold. In some aspects, the decrease of the $EC_{50}$ for the at least one musk compound for a musk olfactory receptor is 4 fold to 2.5 fold. In some aspects, the decrease of the $EC_{50}$ for the at least one musk compound for a musk olfactory receptor is 4 fold to 3 fold. In some aspects, the decrease of the $EC_{50}$ for the at least one musk compound for a musk olfactory receptor is 4 fold to 3.5 fold.

In some aspects, the perfuming composition is incorporated into a consumer product.

In some aspects, the musk olfactory receptor is the OR5AN1 olfactory receptor.

In one aspect, the at least one musk compound is selected from the group consisting of: muscone, MUSCENONE®, exaltone, exaltenone, exaltolide, habanolide, musk xylol, musk ketone, tonalide, vulcanolide, galaxolide, musk DTI, cashmeran, muscenone delta, romandolide, and helvetolide.

In one aspect, the at least one musk compound is selected from the group consisting of: muscone, muscenone delta, musk xylol, and musk ketone.

Products and Formulations According to Some Aspects Presented Herein

In some aspects, the present disclosure provides a perfuming composition,
wherein the perfuming composition comprises at least one musk compound,
wherein the composition comprises at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E, and
wherein the amount of the at least one musk olfactory receptor inhibitor in the perfuming composition is below an amount effective to decrease the $EC_{50}$ for the at least one musk compound for a musk olfactory receptor in a subject.

In one aspect, the above perfuming composition further comprises at least one compound of Formula (I), wherein the at least one compound of Formula (I) is a positive allosteric modulator of a musk olfactory receptor.

In some aspects, the present disclosure provides a perfuming composition,
wherein the perfuming composition comprises at least one musk compound, and wherein the composition does not comprise at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E.

In one aspect, the above perfuming composition further comprises at least one compound of Formula (I), wherein the at least one compound of Formula (I) is a positive allosteric modulator of a musk olfactory receptor.

In some aspects, the present disclosure provides a perfumed consumer product comprising at least one compound of Formula (I) in an amount sufficient to convey, enhance, improve or modify the intensity and/or sensitivity of the perception of the musk odor in the subject. In some aspects, the perfumed consumer product is selected from the group consisting of: air care products, home care products and laundry care products.

In some aspects, the present disclosure provides a perfumed consumer product comprising at least one musk compound and at least one compound of Formula (I) in an amount sufficient to convey, enhance, improve or modify the intensity and/or sensitivity of the perception of the musk odor in the subject. In some aspects, the perfumed consumer product is selected from the group consisting of: air care products, home care products and laundry care products.

It is understood by a person skilled in the art that the at least one compound of Formula (I), as defined herein, may be added into composition described herein in neat form, or in a solvent. Alternatively, the at least one compound of Formula (I) may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof. Alternatively, the at least one compound of Formula (I) may be chemically bound to substrates which are adapted to release the compounds upon application of an exogenous stimulus such as light, enzymes, or the like.

Accordingly, some aspects presented herein provide a composition comprising:
a. at least one compound of Formula (I);
b. at least one ingredient selected from the group consisting of a perfumery carrier and a perfumery base; and
c. optionally at least one perfumery adjuvant.

In some aspects, the perfumed consumer product comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate. For the compositions which comprise both a perfumery carrier and a perfumery base, other suitable perfumery carriers than those previously specified, can be also ethanol, water/ethanol mixtures, limonene or other terpenes, isoparaffins such as those known under the trademark I$_{sopar}$® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

As used herein, the term "perfumery base" refers a composition comprising at least one perfuming co-ingredient. A perfuming co-ingredient does not include a compound of Formula (I). As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Accordingly, in some aspects, the present disclosure provides a perfumed consumer product comprising an effective amount of at least one compound of Formula (I). In some aspects, the perfumed consumer product is selected from the group consisting of: air care products, home care products and laundry care products.

In some aspects, the perfumed consumer product comprising an effective amount of at least one compound of Formula (I) comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

The proportions in which the at least one compound of Formula (I) can be incorporated into the various aforementioned products or compositions vary within a wide range of values. These values are dependent on the nature of the consumer product and on the desired organoleptic effect as well as the nature of the co-ingredients in a given composition when the at least one compound of Formula (I) are mixed with other ingredients, solvents or additives commonly used in the art.

In general, for example, in the case of perfuming compositions, typical concentrations are in the order of 0.001% to 5% by weight, or even more, of compounds of Formula (I), based on the weight of the composition into which they are incorporated. Concentrations lower than these, such as in the order of 0.01% to 100% by weight, can be used when the compositions described herein are incorporated into consumer products, the percentage being relative to the weight of the consumer product.

Accordingly, in some aspects, the present disclosure provides a perfumed consumer product,
wherein the perfuming composition comprises at least one musk compound, and
wherein the composition does not comprise at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E.

Accordingly, one aspect presented herein provides a perfuming composition,
wherein the perfuming composition comprises at least one musk compound,
wherein the composition comprises at least one musk olfactory receptor inhibitor selected from the group consisting of: (E)-2-tridecenol, (E)-2-tridecenoic acid, (E)-2-dodecenoic acid, (E)-2-undecenoic acid, (E)-3-(2-methoxyphenyl)prop-2-enal, pentyl valerate, 3-(3-propan-2-ylphenyl)butanal, (+)-(2E)-4-[(3S)-2,3-dimethyltricyclo[2.2.1.0~2,6~]hept-3-yl]-2-butenal, trans-5-(4-tert-butylphenyl)-2-methylpent-2-enal, octanal, amandolene pur, citrathal, furfuryl mercaptan, bacdanol, (+−)-(2E)-3-(2-methylspiro[5.5]undec-2-en-1-yl) acrylaldehyde, sandenol, (E)-2-hexenal, (Z)-6-nonen-1-ol, 3-phenylpropanal, (E)-2-(Z)-6-nonadien-1-ol, (E)-dec-4-enal, and aldehyde E, and
wherein the amount of the at least one musk olfactory receptor inhibitor in the perfuming composition is below an amount effective to decrease the $EC_{50}$ for the at least one musk compound for a musk olfactory receptor in a subject.

In some aspects, the perfumed consumer product is selected from the group consisting of: air care products, home care products and laundry care products.

In some aspects, the perfumed consumer product comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

Non-limiting examples of suitable perfuming consumer product include:
a perfume, such as a fine perfume, an Eau de Toilette, a cologne or an after-shave lotion;
a fabric care product, such as a liquid detergent, a powder detergent, detergent tablets, a detergent bar, a detergent paste, a detergent pouch, a liquid fabric softener, fabric softener sheets, a fabric scent booster, a laundry pre-treatment, a fabric refresher, an ironing water, a laundry bleach, a carpet powder or a carpet cleaner;
a hair care product, such as a shampoo, a hair conditioner, a hair cream, a hair oil, a hair styling product (such as a spray, mousse or gel), a hair coloration product or a hair permanent wave product;
a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
a skin-cleansing product, such as a soap bar, a shower gel, a liquid hand soap, a bath foam or an intimate wash product;
an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or
a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

In some aspects, the consumer product is selected from the group consisting of: a fine perfume, a splash or eau de perfume, a cologne, an shave or after-shave lotion, a liquid or solid detergent, a fabric softener, a fabric refresher, an ironing water, a paper, a bleach, a carpet cleaners, curtain-care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, and a car care product.

The present invention is best illustrated but is not limited to the following examples.

EXAMPLES

Example 1: Identification of a Musk Olfactory Receptor

The musk compounds muscone, MUSCENONE®, musk xylol and musk ketone formed a highly correlated group with respect to mean odor detection thresholds at the sensory level. To test whether the sensory correlation observed between the four musk compounds was linked to a single odorant receptor's activity, the response of the OR5AN1 olfactory receptor to musk compounds was evaluated. The receptor specificity and the sensitivity values observed were compared to the human psychophysical (sensory) odor detection threshold data (FIG. 1).

The OR5AN1 olfactory receptor was specifically activated by the by muscone, MUSCENONE®, musk xylol and musk ketone. However, none of the other musk compounds tested were able to activate the OR5AN1 olfactory receptor. See FIG. 1a.

The observed musk receptor (FIG. 1a) and psychophysical (FIG. 1b) activity rankings were the same when considering the Pearson correlation for the mean or the median odor detection threshold values (sensory outcome) obtained for the musk compounds with either the ligand potency ($EC_{50}$ values) or efficacy (maximum span) of OR5AN1 olfactory receptor activity.

The psychophysical measures showed a strong direct correlation with $EC_{50}$ and an even stronger correlation with the efficacy (r=0.87 and r=−0.91, respectively)) with the median odor detection thresholds. Similar correlation values were obtained with the mean odor detection thresholds. Both the median and the average sensitivity obtained at the group level followed the potency and the efficacy ranking obtained in vitro (Table 1).

In other words, the receptor activation profile fully recapitulated the psychophysical data and was sufficient to explain the observed sensory correlation between musk compounds.

TABLE 1

Musk ranking by pharmacological potency on OR5AN1 and perceptual detection threshold.

| Rank order | Odorant name | EC50 [a] Log(M) | Span [b] (HTRF ratio) | Median odor detection threshold Log(μmol/l air) | Mean odor detection threshold Log(μmol/l air) |
|---|---|---|---|---|---|
| 1. | Musk ketone | $2.56e^{-8}$ | 4312 | $6.41e^{-9}$ | $6.11e^{-9}$ |
| 2. | Musk xylol | $3.57e^{-7}$ | 4217 | $1.02e^{-8}$ | $2.20e^{-8}$ |
| 3. | Muscenone ® | $2.01e^{-6}$ | 3629 | $1.04e^{-7}$ | $1.26e^{-7}$ |
| 4. | Muscone | $3.29e^{-6}$ | 2979 | $1.09e^{-6}$ | $1.21e^{-6}$ |

[a] EC50 Pearson correlation to Median, r = 0.866177 and to Mean, r = 0.869362
[b] Span Pearson correlation to Median, r = −0.91012 and to Mean, r = −0.91267

Example 2: Identification of Musk Olfactory Receptor Enhancers 481 binary mixtures were created by mixing a MUSCENONE® stock solution with a stock solution of each test compound to a final concentration 10 and 500 μM, respectively.

Figure 2:
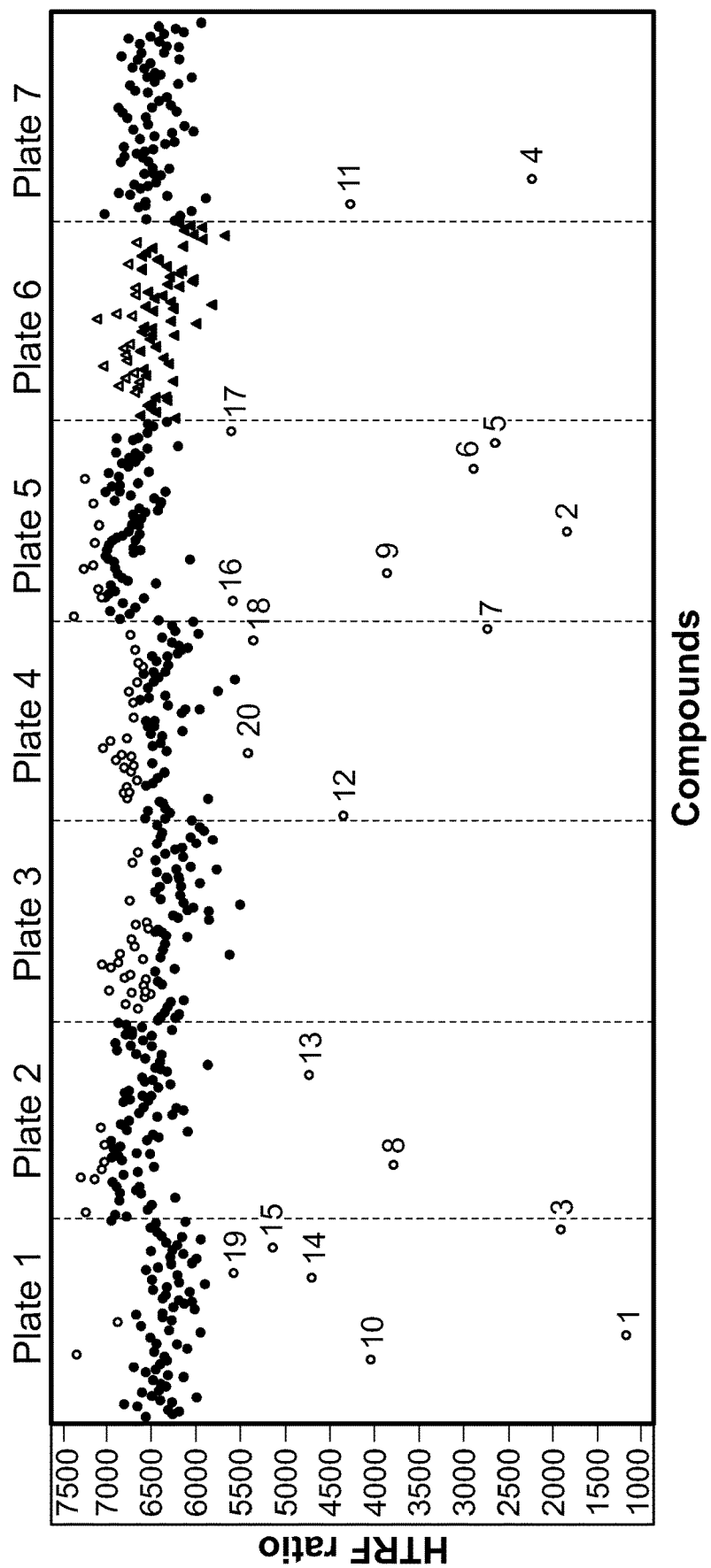
FIG. 2 shows the result of a single point binary mixture of MUSCENONE® and perfumery raw materials screening for OR5AN1 Musk-induced activity enhancement.

Stock solutions were made of compounds dissolved in pure DMSO. Each mixture was presented to a cell line expressing the OR5AN1 olfactory receptor. The final concentration of DMSO in each binary mixture was 0.17%, and had no visible effect on the cells The resulting activation was then measured and compared to MUSCENONE® alone (defining the baseline of the enhancement assay). The quality of the HTS process was determined and the window variability and signal reliability were assessed by calculating the Z' value of each plate. See FIG. 1. Twenty hits were obtained, five of which were macrocyclic ketone and nitromusk OR5AN1 olfactory receptor agonists (hit n° 1, 2, 3, 5 and 9). See FIG. 2 and Table 2. These OR5AN1 olfactory receptor agonists further confirmed that the dynamic range of the assay window was sufficient (as the responses recorded were well above baseline) and thus likely sensitive enough to detect even low levels of putative enhancement.

15 candidates, marked as "enhancement" in Table 2 were identified. Strikingly, 80% of these putative enhancers (12/15) belonged to the same class of chemicals: unsaturated aliphatic aldehydes. Next, two parallel dose-response experiments to confirm the true enhancement properties of the potential candidates were performed. First, a dose-response of each individual candidate was performed to determine if it was an agonist by itself. Second, a MUSCENONE® dose-response curve in the presence and absence of a 250 μM concentration of the putative modulator was assessed for $EC_{50}$ shifts. Molecules that increased the response of the OR5AN1 olfactory receptor to MUSCENONE® but did not display measurable intrinsic agonist activity themselves were considered to be true enhancers and were selected for further studies.

TABLE 2
Compounds selected from the enhancement screen, numbered by decreasing OR5AN1 activity (span).
| | Molecules | Hit Type |
|---|---|---|
| 1 | 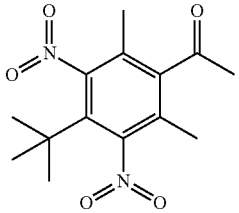 [SMILES: CC(=O)c1c(C)c([N+](=O)[O-])c(C(C)(C)C)c([N+](=O)[O-])c1C]<br>Musk Ketone Pur | Agonist |
| 2 | 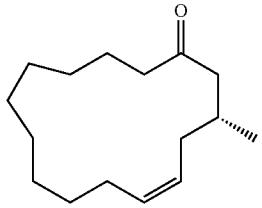 [SMILES: C[C@@H]1C/C=C\CCCCCCCCCC(=O)C1]<br>Dextro Muscenone | Agonist |
| 3 | 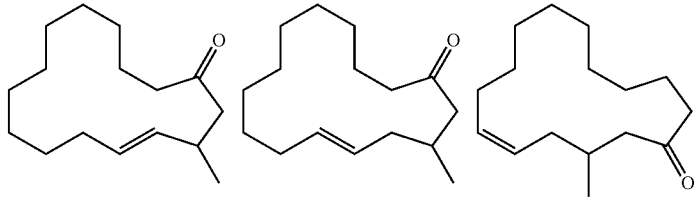<br>Muscenone Delta | Agonist |
| 4 | 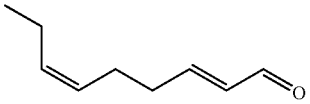<br>Pelargodienal | Enhancement |
| 5 | 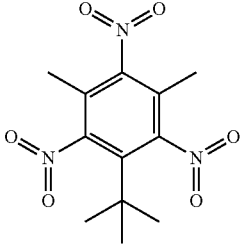 [SMILES: Cc1c([N+](=O)[O-])c(C)c([N+](=O)[O-])c(C(C)(C)C)c1[N+](=O)[O-]]<br>Musc X | Agonist |
| 6 | 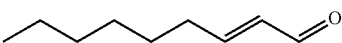<br>Nonylenic Aldehyde | Ehancement |
| 7 | 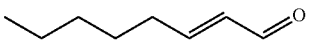<br>2-Octenal | Agonist |
| 8 | 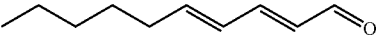<br>E2,E4-Decadienal | Enhancement |

TABLE 2-continued

Compounds selected from the enhancement screen, numbered by decreasing OR5AN1 activity (span).

| | Molecules | Hit Type |
|---|---|---|
| 9 | Muscone Laevo | Agonist |
| 10 | Dodecenal | Enhancement |
| 11 | 2-Decenal | Enhancement |
| 12 | N 302 | Enhancement |
| 13 | Tridecylenic Aldehyde | Enhancement |
| 14 | Nonadienal dea | Enhancement |
| 15 | 2-Hexenal | Enhancement |
| 16 | Amadolene Pur | Enhancement |

TABLE 2-continued

Compounds selected from the enhancement screen, numbered by decreasing OR5AN1 activity (span).

| | Molecules | Hit Type |
|---|---|---|
| 17 | 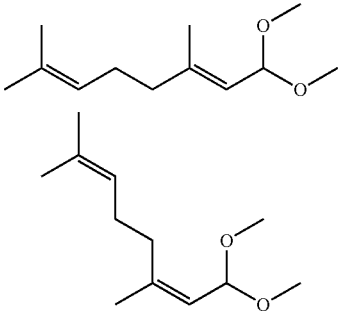<br>Citral Dimethylacetal | Enhancement |
| 18 | 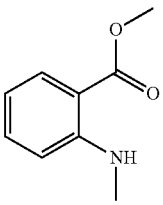<br>Methyl n-Methylanthranilate | Enhancement |
| 19 | 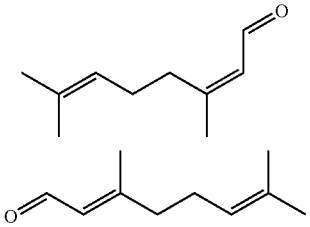<br>Neral & Geranial | Enhancement |
| 20 | 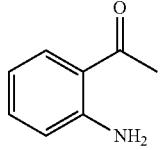<br>Ortho Aminoacetophenone | Enhancement |

From this analysis, the volatile tridecylenic aldehyde (TDA), an aliphatic α-β mono-unsaturated aldehyde was identified. This compound did not activate the OR5AN1 olfactory receptor by itself but in combination with MUSCENONE® yielded a clear enhancement effect compared to MUSCENONE® alone. See FIG. 3.

Figure 3A:
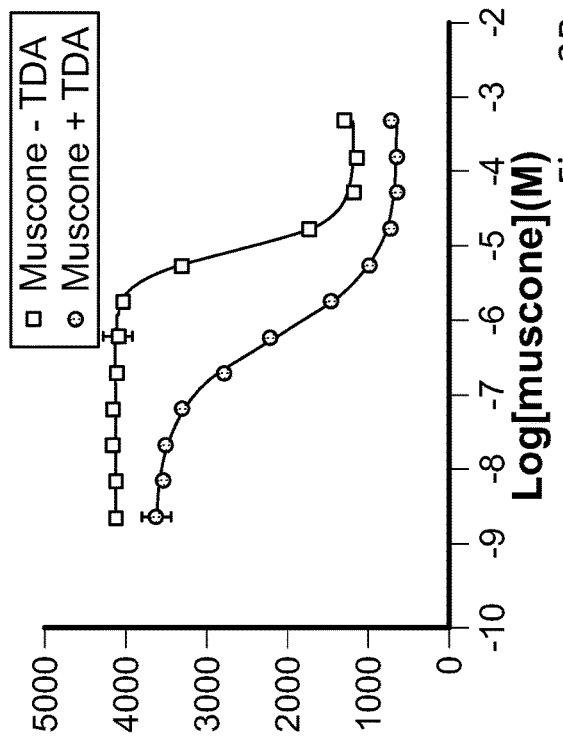
FIG. 3 shows the dose response curves of OR5AN1 to all four of agonist Muscone, MUSCENONE®, Musk X and Musk ketone in the presence and absence of tridecylenic aldehyde, and a dose-response to tridecylenic aldehyde alone.

Tridecylenic aldehyde appeared to be an effective enhancer of the OR5AN1 olfactory receptor. The addition of TDA at 250 μM led to a drastic reduction in the MUSCENONE® $EC_{50}$ (an approximate 21 fold shift) and to an overall greater maximal activation level (increased span) (FIG. 3a). When tested by itself, TDA did not display any significant activity aside from very minor binding activity above approximately 100 μM. At this concentration, the binding of TDA yielded an activation of less than 8% of the MUSCENONE® activation window. Tridecylenic aldehyde is therefore not considered a true agonist of OR5AN1.

Figure 3B:
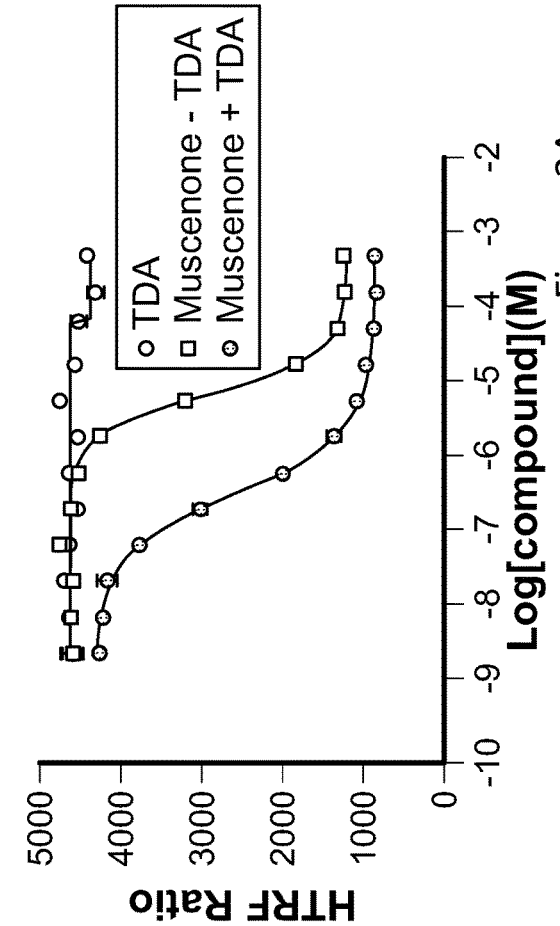
Figure 3C:
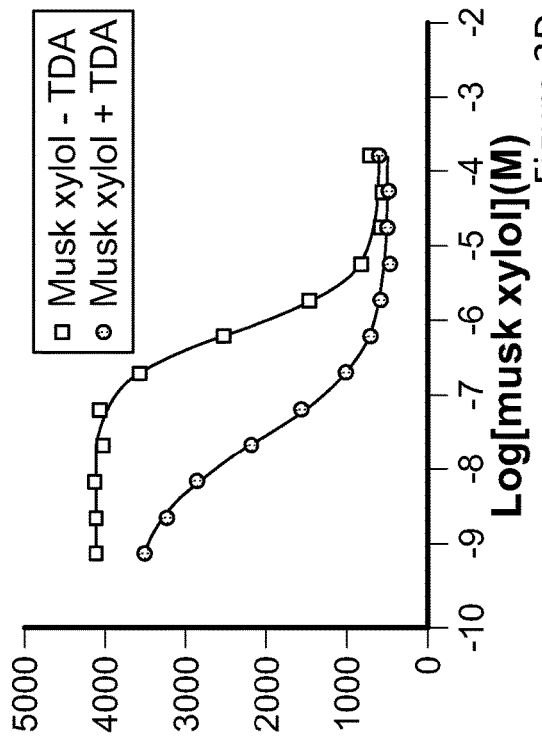
Figure 3D:
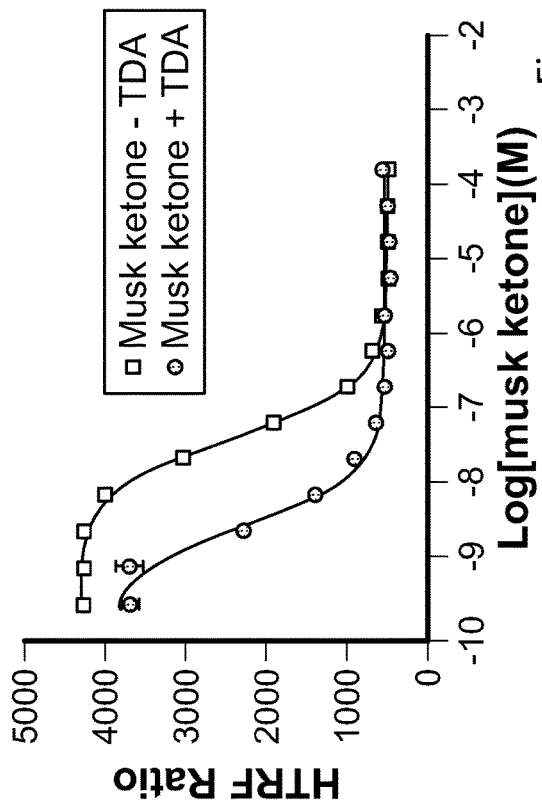

The effect of TDA on musk compound-induced activation of the OR5AN1 olfactory receptor was observed with muscone, musk xylol and musk ketone. All agonists exhibited comparable leftward dose-response curve shifts in the presence of a 250 μM concentration of TDA (FIG. 3b-d). This indicated that the enhancement was mediated through a receptor binding event and not likely mediated by OR5AN1-independent effects such as on the assay cells themselves. The decrease in $EC_{50}$ ranged between 13 and 28 fold in repeat experiments (FIG. 4). The apparent enhancement observed with binary mixtures of musk and TDA is inconsistent with a binding of competitive nature, mainly because TDA, which is not an agonist, also does not act as an antagonist. Rather, this type of data is indicative of a non-competitive binding site for TDA.

Tables 3a and 3b below reports the effect of additional compounds on the $EC_{50}$ and span of MUSCENONE®.

TABLE 3a

| | | $EC_{50}$ (Potency Fold Shift) Concentration of Enhancer (µM) | | |
|---|---|---|---|---|
| | Compound (Enhancer) | 600 | 200 | 66.6 |
| 1 | (2E)-7,8-dimethyl-2,7-nonadienal | 3.99 | 9.03 | 1.52 |
| 2 | methyl(5E)-7-oxo-5-heptenoate | 4.29 | 2.16 | 1.18 |
| 3 | (2E)-7-methyl-2,6-octadienal | 29.14 | 5.60 | 1.36 |
| 4 | (2E)-6,6-dimethyl-2-heptenal | 6.88 | 3.30 | 1.15 |
| 5 | (+−)-(2E)-5,9-dimethyl-2,8-decadienal | 9.07 | 9.56 | 1.84 |
| 7 | (E)-2-tetradecenal | 7.13 | 5.06 | 3.34 |
| 8 | 4-hydroxy-2-nonenal | 4.99 | n/a | 1.30 |
| 9 | Trans-2,6,7-dimethyl-2,6-octadienal | n/a | 4.47 | 1.18 |

TABLE 3b

| | | Span (Efficacy Fold Shift) Concentration of Enhancer (µM) | | |
|---|---|---|---|---|
| | Compound (Enhancer) | 600 | 200 | 66.6 |
| 1 | (2E)-7,8-dimethyl-2,7-nonadienal | 1.24 | 1.31 | 1.07 |
| 2 | methyl(5E)-7-oxo-5-heptenoate | 1.18 | 1.15 | 0.99 |
| 3 | (2E)-7-methyl-2,6-octadienal | 1.18 | 1.20 | 1.06 |
| 4 | (2E)-6,6-dimethyl-2-heptenal | 1.14 | 1.02 | 1.06 |
| 5 | (+−)-(2E)-5,9-dimethyl-2,8-decadienal | 1.15 | 1.22 | 1.02 |
| 7 | (E)-2-tetradecenal | 1.04 | 1.00 | 0.94 |
| 8 | 4-hydroxy-2-nonenal | 1.09 | 1.32 | 1.00 |
| 9 | Trans-2,6,7-dimethyl-2,6-octadienal | 1.03 | 1.13 | 1.05 |

Example 3: Tridecylenic Aldehyde Acts as a Positive Allosteric Modulator (PAM) to Enhance OR5AN1 Olfactory Receptor Activity Functional dose-response experiments were performed to reveal the allosteric nature of the interaction between tridecylenic aldehyde (TDA) and the OR5AN1 olfactory receptor. The level of enhancement of the OR5AN1 olfactory receptor activation was evaluated at distinct concentrations of the enhancer. Using the same cell-based assay described in Example 2, dose response curves of OR5AN1 to MUSCENONE® in the presence of serial concentrations of tridecylenic aldehyde spanning from 0 to 1 mM were performed. The curves were obtained by applying the simplified Allosteric $EC_{50}$ shift effect equation (available in Prism5, v. 5.02) derived from the ternary complex interaction model. The enhancement levels recorded were not linearly dependent on the concentration of the enhancer, and the following key parameters values for a (the cooperativity factor) and $K_B$ (the equilibrium dissociation constant of TDA) were obtained from the model: $\alpha=15.7$ and $K_B=259$ µM. $\alpha$ greater than 1 is indicative positive allosteric modulation. Following this method, 2-decenal and nonylenic aldehyde, two potent enhancers, exhibited allosteric modulation properties similar to TDA.

Full pharmacological characterization of the enhancers provides a means to rank order the enhancers based on 1) the potency shift they induce when combined with a perfumery ingredient (e.g. musky, floral or woody ingredients), 2) the efficacy (the activity level of the target receptor) increase compared to the efficacy observed with the compound alone, 3) the affinity of the enhancing compound for the receptor, 4) the minimal concentration necessary for enhancement to occur, and/or 5) or the most efficient ratio of enhancer to perfumery compound that leads to the greatest enhancement performance.

Figure 5A:
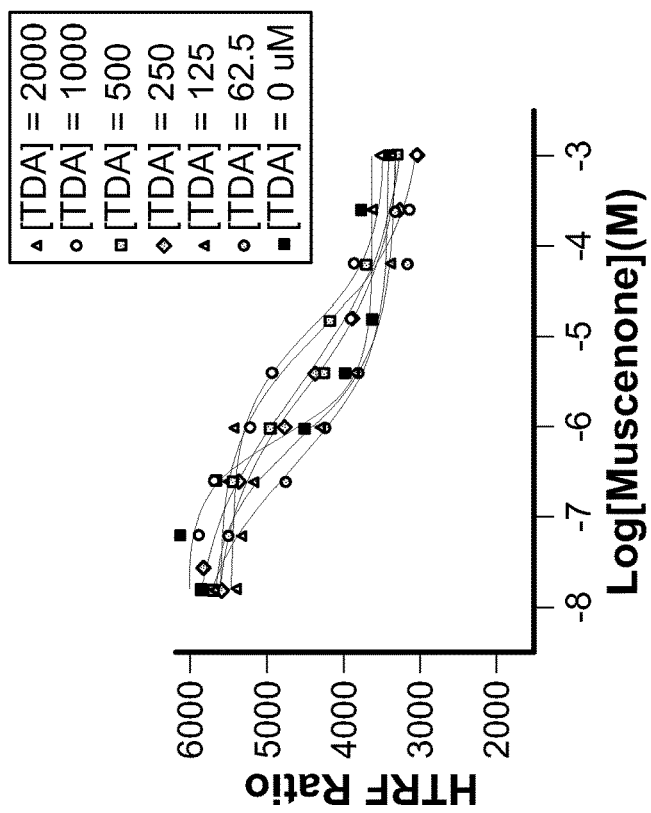
FIG. 5 displays a series of dose response curves of OR5AN1 to MUSCENONE® in the presence of serial concentrations of tridecylenic aldehyde and also indicates the calculated log values for the cooperativity factor α and the equilibrium constant $K_B$.
Figure 5B:
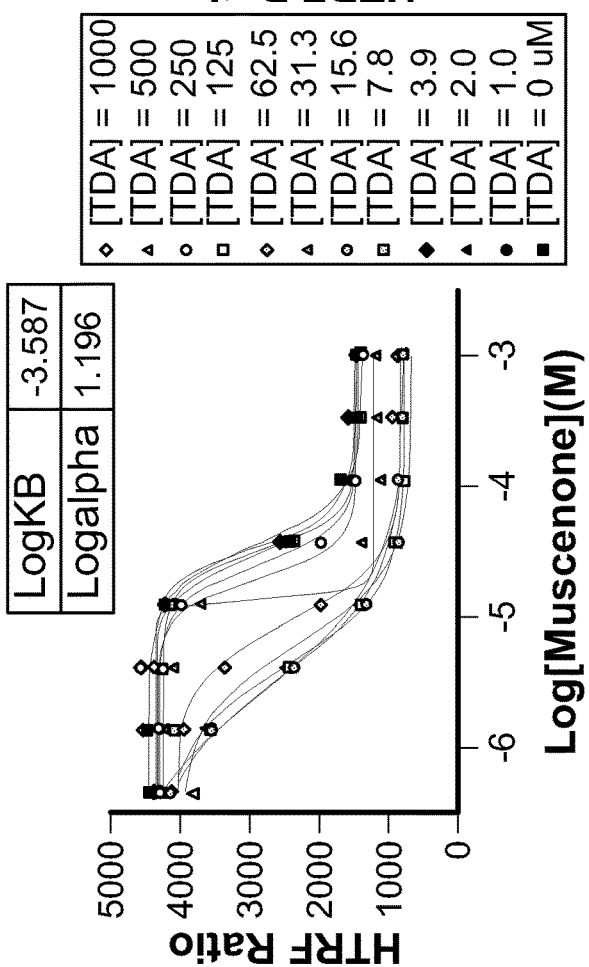

Furthermore and as a control, a similar experiment was performed on the mouse MUSCENONE® responsive odorant receptor Olfr1440, the ortholog of OR5AN1. Tridecylenic aldehyde did not enhance the activity of the Olfr1440 receptor. Rather, the aldehyde led to a slight inhibition of the Olfr1440 MUSCENONE®-induced activation (FIG. 5). This further supports the view that enhancement of OR5AN1 by tridecylenic aldehyde is receptor-mediated and receptor-specific.

Example 4: The Structure-Activity Relationship of Positive Allosteric Modulators of the OR5AN1 Olfactory Receptor A chemically diverse set of 67 volatile compounds structurally related to the aliphatic unsaturated aldehydes found initially (see Example 1 and FIG. 1) was generated for structure-activity-relationship (SAR) analysis. The sixty-seven molecules were tested for their enhancement of the OR5AN1 olfactory receptor to characterize the necessary chemical requirements.

Dose response curves to MUSCENONE® were obtained in the presence of 250 µM of each compound and compared to a dose-response curve of MUSCENONE® alone. The resulting enhancement was quantified by means of $EC_{50}$-fold shift (potency increase) and the efficacy span ratio (efficacy increase).

The $EC_{50}$-fold shift was obtained by dividing the $EC_{50}$ of MUSCENONE®+compound by the reference $EC_{50}$ MUSCENONE® alone. The span ratio was obtained by dividing the span of MUSCENONE®+compound by the reference span of MUSCENONE® alone. Specifically, diverse aliphatic $\alpha$-$\beta$ mono- or poly-unsaturated molecules have been compared.

$\alpha$-$\beta$-mono-unsaturated di-substituted aliphatic aldehydes were systematically found to exhibit the most potent enhancement. Functional group replacement, saturation modification and additional substitutions appear to reduce or eliminate the potential of that compound to enhance the receptor (FIGS. 6, 8-12). Additional modifications around the $\alpha$-$\beta$ mono-unsaturated aliphatic aldehydes such as substitution at the a position or cyclisation of the aliphatic tail prevented enhancement effects to take place.

Figure 7:
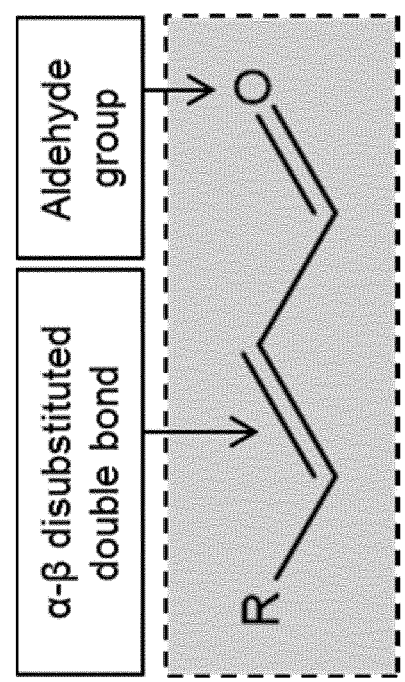
FIG. 7 depicts the chemical requirements identified from the SAR analyses that elicit OR5AN1 Musk response enhancement according to certain aspects presented herein.
Figure 8B:
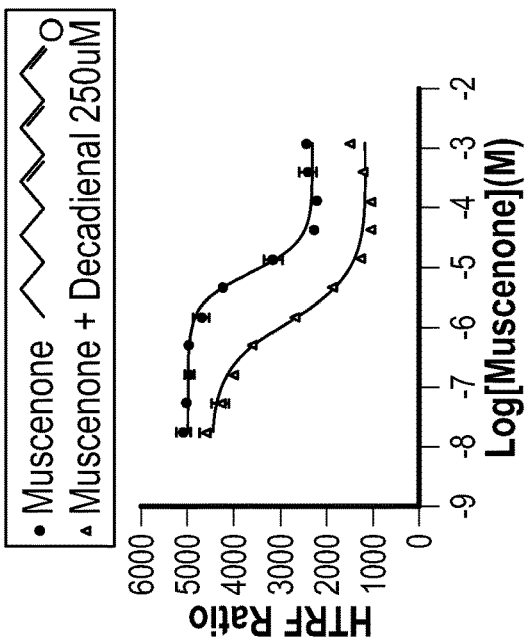
FIG. 8 shows the distinct enhancement levels obtained with decenal, decadienal and decanal.
Figure 8C:
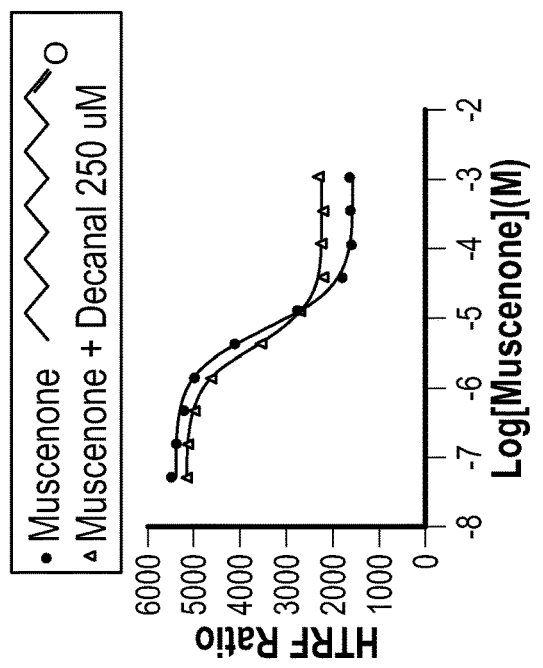
Figure 8A:
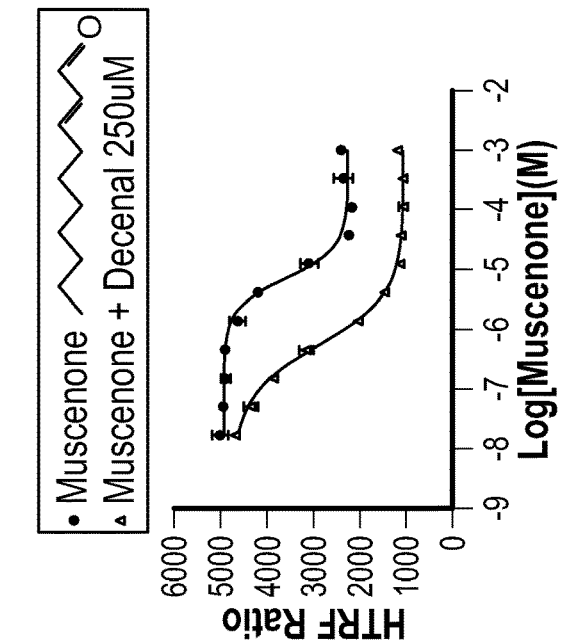
Figure 9B:
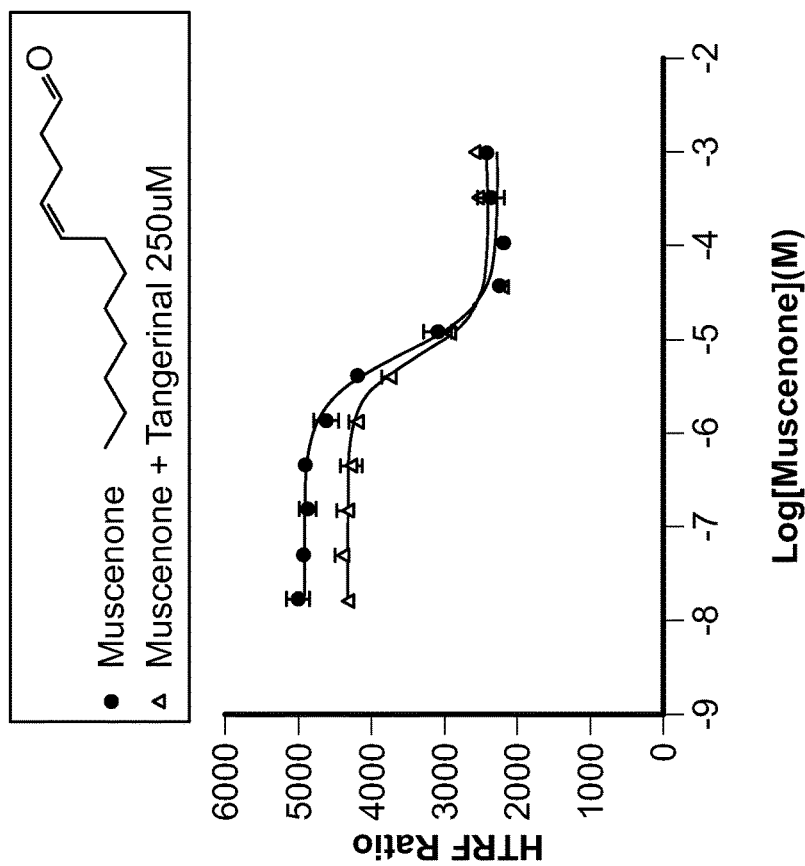
FIG. 9 shows the distinct enhancement levels obtained with dodecenal and tangerinal.
Figure 9A:
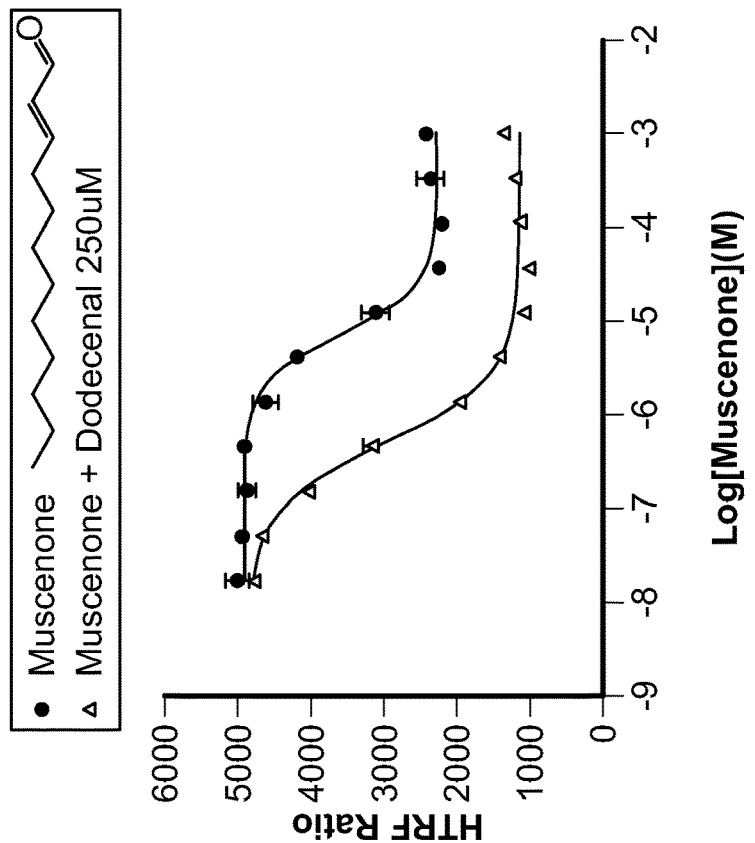

A resulting generic chemical structure showing the required chemical features for specific OR5AN1 enhancing has been determined (FIG. 7). Pairwise comparisons of the dose-response curves obtained with the $\alpha$-$\beta$-mono-unsaturated aldehydes and derived saturational or functional isomers further examplifies the necessary chemical features required for OR5AN1 enhancement (FIGS. 8-12). FIG. 8 shows the distinct enhancement levels obtained with decenal, decadienal and decanal, and the requirement of the unsaturation. FIG. 9 shows the distinct enhancement levels obtained with dodecenal and tangerinal, and the importance of the unsaturation position.

Figure 11B:
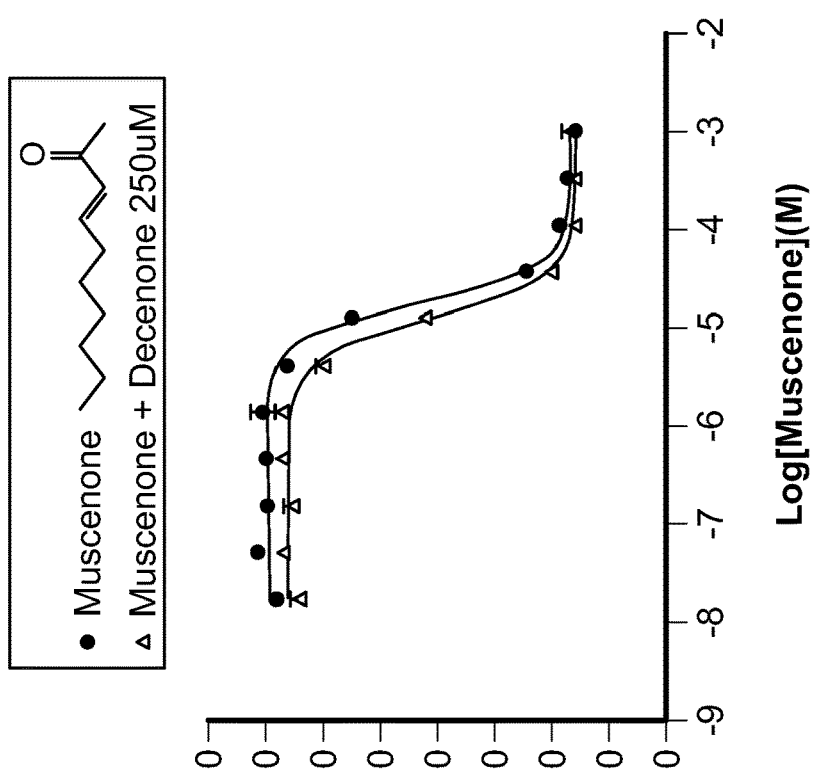
FIG. 11 shows the distinct enhancement levels obtained with decenal and decenone, and the absence of enhancement with a ketone functional group.
Figure 11A:
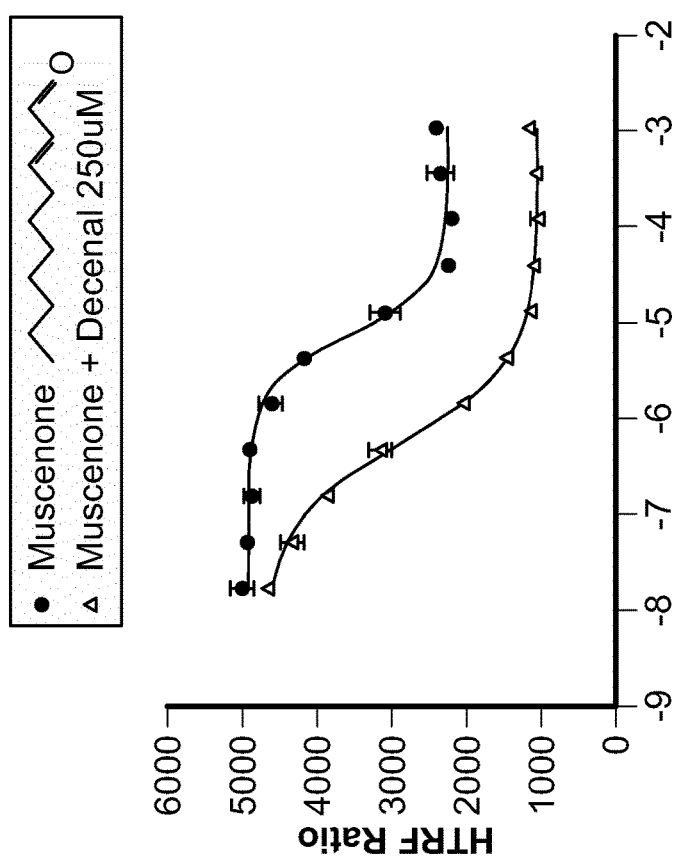
Figure 12B:
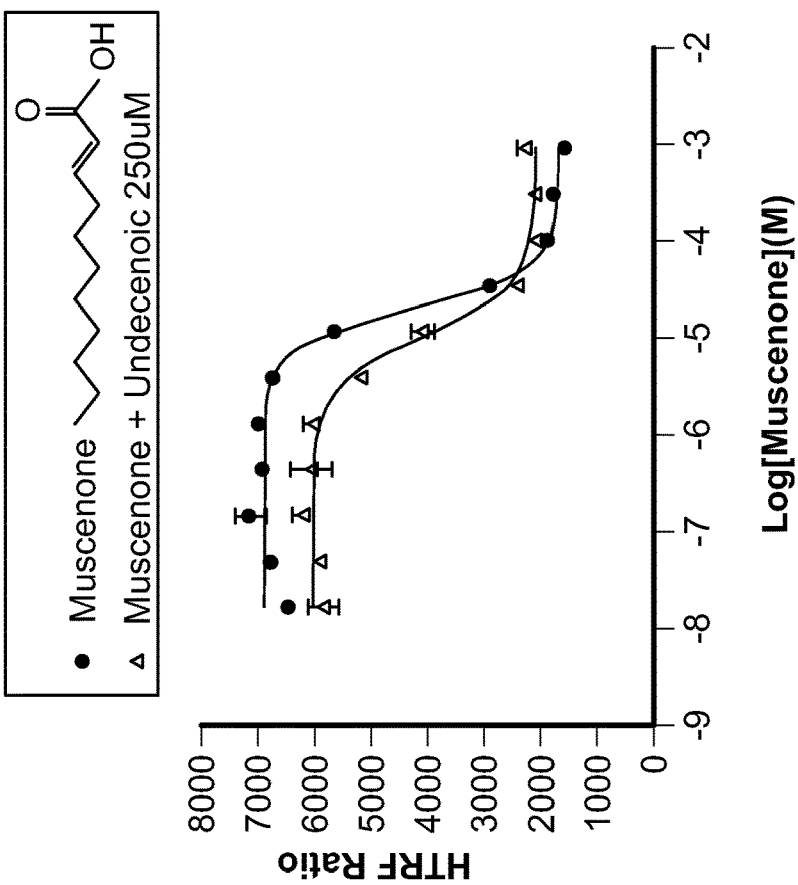
FIG. 12 shows the distinct enhancement levels obtained with undecenal and undecenoic acid, and the absence of enhancement with an acid group.
Figure 12A:
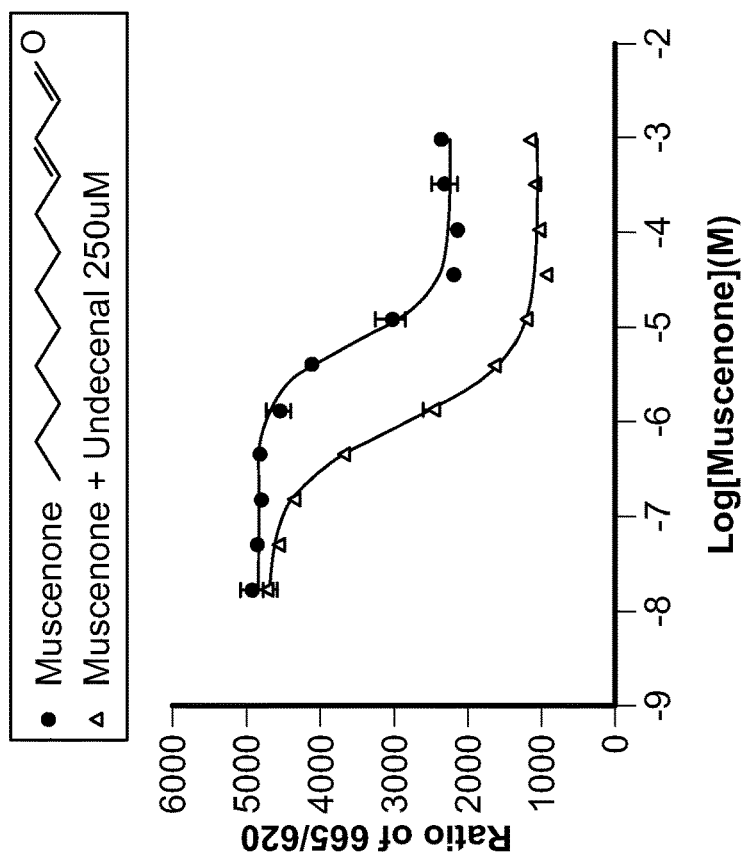

FIG. 10 shows the distinct enhancement levels obtained with nonylenic aldehyde, nonenol and nordecenol, and the absence of enhancement when an alcohol functional group is used instead of an aldehyde group. FIG. 11 shows the distinct enhancement levels obtained with decenal and decenone, and the absence of enhancement when a ketone functional group is used. FIG. 12 shows the distinct enhancement levels obtained with undecenal and undecenoic acid, and the absence of enhancement when an acid functional group is used.

A SAR study was conducted to identify the best enhancers and determine the chemical requirements needed to enhance a given receptor. In the case of the OR5AN1 olfactory receptor, at least 10 potent enhancers have been identified, all of which are volatile compounds applicable to perfumery creation/design. Without intending to be limited to any particular theory, when several enhancers are at hand for creation, a subsequent organoleptic characterization of their inherent smell further allows selecting the volatiles compounds that best fit downstream applications with respect to the overall tonality of the application (i.e. a perfume). In other words, an enhancing ingredient portfolio corresponding to each target molecule, for example, musk, is generated and provides perfumers with more creation tools.

Figure 13A:
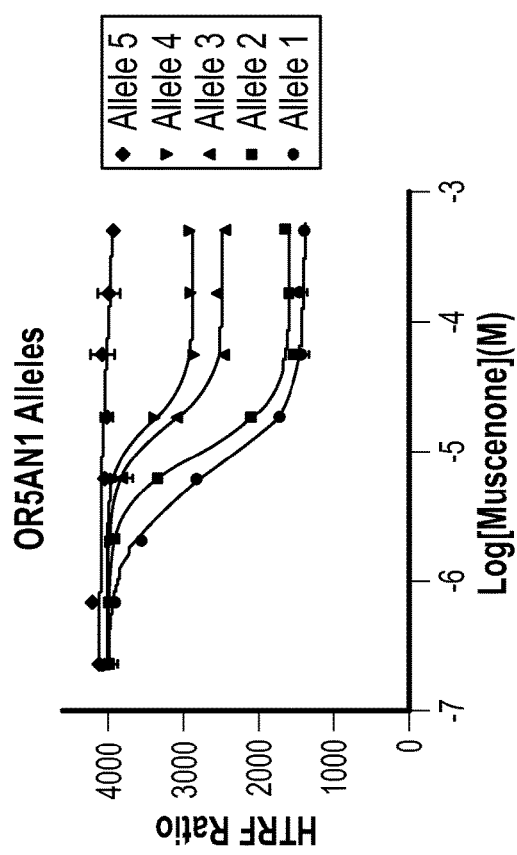
FIG. 13 shows OR5AN1 alleles are not functionally equivalent when activated with MUSCENONE® but enhancement restores activity of hypofunctional alleles.
Figure 13C:
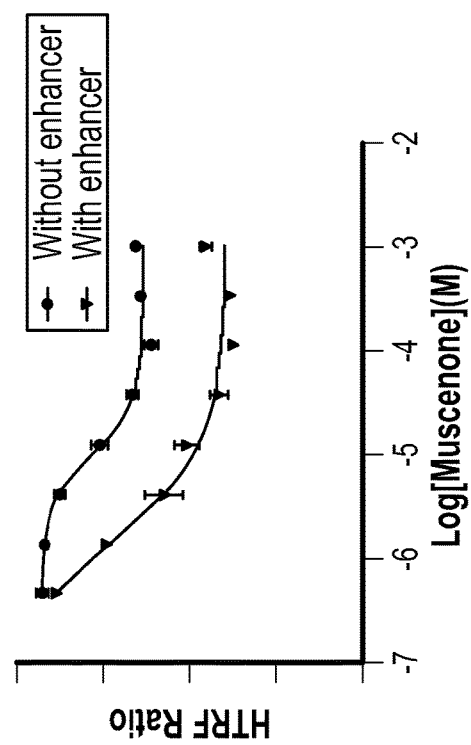
Figure 13B:
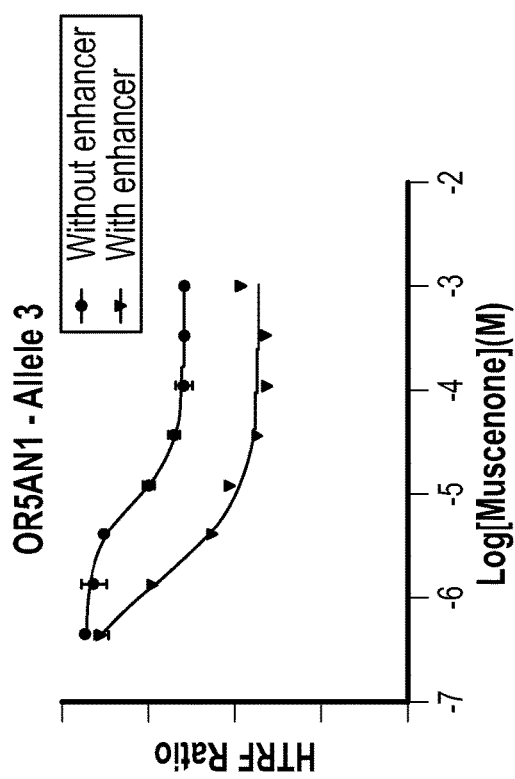

Example 5: Hypofunctional OR Alleles can be Restored in the Presence of an Enhancer Olfactory receptors are frequently encoded by several alleles for any given OR gene, from a single allele to over fifteen alleles. Five OR5AN1 alleles are known to be present in human populations. These alleles are functionally not equivalent and exhibit distinct activity levels ranging from fully functional (allele 1 and 2), hypofunctional (allele 3 and 4) to loss-of function (allele 5) (FIG. 13).

Testing the hypofunctional OR5AN1 allele 3 and 4 in a cell based assay in the presence and in the absence of the identified enhancer tridecylenic aldehyde showed a substantial increase in the activity level. The observed $EC_{50}$ value for allele 3 exhibited a 6.0 fold shift (from 9.0 µM to 1.5 µM in the presence of 250 µM tridecylenic aldehyde) and an activity span-ratio of 2.02 (with an activity increase from 2311 to 4663 relative fluorescent HTRF units in the presence of tridecylenic aldehyde). The observed $EC_{50}$ value for allele 4 exhibited a 6.25 fold shift (from 10.1 µM to 1.6 µM in the presence of 250 µM tridecylenic aldehyde) and an activity span-ratio of 2.16 (with an activity increase from 2328 to 5026 relative fluorescent HTRF units in the presence of tridecylenic aldehyde). Both potency and efficacy shifted favorably and lead to an activity level more comparable to the presumably stronger activity elicited by MUSCENONE® for people carrying allele 2. These data suggest that individuals carrying these alleles may be more sensitive to a perfumery application containing an OR5AN1 activating musk in the presence of an enhancing perfumery ingredient.

Example 6: Human Sensitivity to a Musk Compound is Increased in the Presence of an Enhancer Sensitivity of human individuals to MUSCENONE® was evaluated by performing an odor detection threshold (ODT) test. The ODT test consisted of identifying the concentration for which 50% of the panelists are able to determine which of three containers contains the target compound Muscenone® in a forced-choice triangle tests. Two tests were performed to calculate the ODT in mixtures containing Muscenone® plus a perceivable background odor of chemically similar molecules a) the enhancer tridecylenic aldehyde and b) the non-enhancing volatile compound, nonanal. These two molecules are chemically similar but nonanal does not exhibit the necessary α-β-unsaturation for enhancement to occur identified in Example 5.

Figure 14:
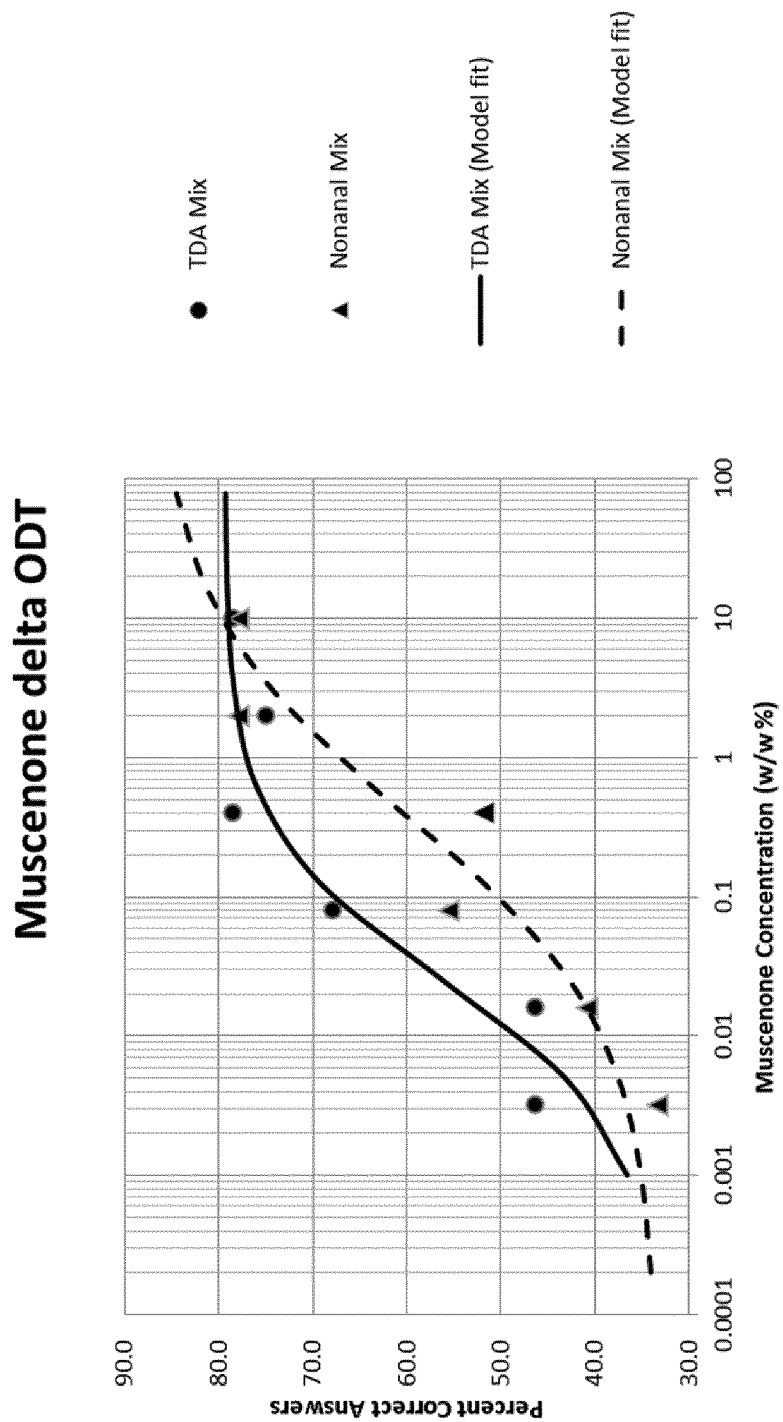
FIG. 14 shows human panelist more sensitive to MUSCENONE® in the presence of an enhancer compared to a non-enhancing compound.

28 panelists were given a series of triangle tests with decreasing concentrations of MUSCENONE® in the presence of tridecylenic aldehyde at a concentration of 0.1%. Within each triangle triangle test, the three samples contained tridecylenic aldehyde at 0.1% and one sample also contained MUSCENONE®. 27 panelists were given a series of triangle tests with increasing concentration of MUSCENONE® in the presence of nonanal at a concentration of 0.1%. Within each triangle test, the three samples contained nonanal at 0.1% and one sample also contained MUSCENONE®. In each triangle test, the panelists were asked to identify the one sample that was different from the other two samples. The ODT was calculated by fitting a non-linear regression model onto the data and calculating the MUSCENONE® concentration at which the proportion of correct responses was equal to ⅔ (the midpoint between chance rate 1/3 and all correct answers 1). There was a lower ODT value when the musk was mixed with the enhancer than with the neutral compound: 0.09% compared to 0.93%, respectively, indicating distinct musk detection levels in experimentally similar conditions (FIG. 14).

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method for modifying an intensity or a sensitivity of a subject's perception of a musk odor, the method comprising,
    contacting a subject with a positive allosteric modulator of formula (I) selected from the group consisting of (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (2E)-7,8-dimethyl-2,7-nonadienal, methyl(5E)-7-oxo-5-heptenoate, (2E)-7-methyl-2,6-octadienal, (2E)-6,6-dimethyl-2-heptenal, (+−)-(2E)-5,9- dimethyl-2,8-decadienal, and (E)-2-tetradecenal;
    wherein the subject is contacted with the positive allosteric modulator in an amount sufficient to modify an intensity or sensitivity of a perception of the musk odor in the subject; and
    wherein the method further comprises contacting the subject with at least one musk compound selected from the group consisting of (R)-3-methylcyclopentadecanone, 3-methyl-5-cyclopentadecen-1-one, 1-(1.1-dimethylethyl)-3,5-dimethyl-2,4,6-trinitro-benzene, and 4-tert-butyl-2,6-dimethyl-3,5-dinitroacetophenone.

2. The method of claim 1, wherein the at least one positive allosteric modulator is incorporated into a perfuming composition.

3. The method of claim 2, wherein the perfuming composition further comprises at least one musk compound.

4. The method of claim 2, wherein the perfuming composition is incorporated into a consumer product.

5. The method of claim 1, wherein the at least one positive allosteric modulator is incorporated into a. consumer product.

6. The method of claim 5, wherein the consumer product further comprises at least one musk compound.

\* \* \* \* \*